US008278083B2

(12) United States Patent
Raviv et al.

(10) Patent No.: US 8,278,083 B2
(45) Date of Patent: Oct. 2, 2012

(54) INACTIVATED INFLUENZA VIRUS COMPOSITIONS

(75) Inventors: Yossef Raviv, Rockville, MD (US); Mathias Viard, Frederick, MD (US); Robert Blumenthal, Bethesda, MD (US); Robert J. Hogan, Athens, GA (US); Stephen Mark Tompkins, Watkinsville, GA (US)

(73) Assignees: The United States of America as represented by the Secretary of the Department of Health and Human Services, Washington, DC (US); University of Georgia Research Foundation, Inc., Athens, GA (US)

( * ) Notice: Subject to any disclaimer, the term of this patent is extended or adjusted under 35 U.S.C. 154(b) by 358 days.

(21) Appl. No.: 12/225,551

(22) PCT Filed: Mar. 23, 2007

(86) PCT No.: PCT/US2007/007338
§ 371 (c)(1),
(2), (4) Date: May 18, 2009

(87) PCT Pub. No.: WO2008/054481
PCT Pub. Date: May 8, 2008

(65) Prior Publication Data
US 2009/0297558 A1    Dec. 3, 2009

Related U.S. Application Data

(63) Continuation-in-part of application No. 11/525,250, filed on Sep. 21, 2006.

(60) Provisional application No. 60/785,781, filed on Mar. 24, 2006, provisional application No. 60/555,268, filed on Mar. 22, 2004.

(51) Int. Cl.
*A61K 39/145* (2006.01)
*C12N 13/00* (2006.01)

(52) U.S. Cl. ............. 435/173.3; 424/209.1; 424/235.1

(58) Field of Classification Search .................. None
See application file for complete search history.

(56) References Cited

U.S. PATENT DOCUMENTS 5,663,043 A * 9/1997 Zepp et al. .................... 435/2

FOREIGN PATENT DOCUMENTS

| WO | WO-9941360 A1 | 8/1999 |
| WO | WO 2005/093049 A1 * | 6/2005 |
| WO | WO-2005093049 A1 | 10/2005 |
| WO | WO-2008054481 A2 | 5/2008 |

OTHER PUBLICATIONS

Salk et al. (J Exp. Med, 1940, vol. 30, p. 729-745).*

"Australian Application Serial No. 2005227320, Office Action Mailed Jan. 6, 2009", 2 pgs.
"International Application Serial No. PCT/US2005/009559, International Search Report mailed Sep. 12, 2005", 9 pgs.
"International Application Serial No. PCT/US2005/009559, Written Opinion mailed Sep. 12, 2005", 6 pgs.
Chanh, T. C, et al., "Neutralization of HIV-1 and inhibition of HIV-1-induced syncytia by 1,8-naphthalimide photoactive compound", *AIDS Res Hum Retroviruses.*, 9(9), (Sep. 1993), 891-6.
Rai, S, et al., "Dramatic improvements in viral inactivation with brominated psoralens, naphthalenes and anthracenes", *Photochem Photobiol.*, 58(1), (Jul. 1993), 59-65.
Chinese Application Serial No. 200580009241.1, Office Action mailed Jul. 18, 2008, 6 pgs.
European Application Serial No. 05760441.5, Office Action mailed Jul. 8, 2008, 5 pgs.
International Application Serial No. PCT/US2007/007338, Search Report mailed Aug. 5, 2008, 8 pgs.
International Application Serial No. PCT/US2007/007338, Written Opinion mailed Aug. 5, 2008, 7 pgs.
Bercovici, T., "5-[125I]Iodonaphthyl Azide, a Reagent to Determine the Penetration of Proteins into the Lipid Bilayer of BiologicalMembranes", *Biochemistry*, 17(8), (Apr. 18, 1978), 1484-1489.
Chanh, T. C, et al., "Neutralization of HIV-1 and Inhibition of HIV-i-Induced Syncytia by 1, 8-Naphthalinnide Photoactive Compound", *AIDS Res Hum Retroviruses*, 9(9), Mary Ann Liebert, Inc., Publishers, (1993), 891-896.
Chanh, T. C, et al., "Photodynamic inactivation of simian immunodeficiency virus", *Journal of Virological Methods*, 26(1), (1989), 125-131.
Gruenert, D. C., et al., "Repair of ultraviolet damage in human cells also exposed to agents that cause strand breaks, crosslinks, monoadducts and alkylations", *Chem Biol Interact.*, 33(2-3), (Jan. 1981), 163-77.
Hanson, C. V, "Rapid Photochemical Inactivation of Human Immunodeficiency Virus HIV", *Journa of Cellular Biochemistry, Supplement #11 Part D. Symposium on Human retroviruses, cancer and aids: Approaches to prevention and therapy.*, (1987), 65.
Merezhinskaya, Natasha, "Reversible penetration of x-glutathione S-transferase into biological membranes revealed by photosensitized labelling in situ", *Biochem J. 335*, (1998), 597-604.
Moreno, G., et al., "Photosensitization of mammalian cells by psoralens and porphyrins", *Biochimie.*, 68(6), (Jun. 1986), 869-73.
Pak, Charles C., et al., "Conformational Changes and Fusion Activity of Vesicular Stomatitis Virus Glycoprotein: [125I]Iodonaphthyl Azide Photolabeling Studies in Biological Membranes", *Biochemistry*, 36(29), (Jul. 22, 1997), 8890-8896.

(Continued)

*Primary Examiner* — Agnieszka Boesen
(74) *Attorney, Agent, or Firm* — Woodcock Washburn LLP

(57) ABSTRACT

The invention provides compositions of inactivated influenza virus that can be used as vaccines and immunological compositions useful for inhibiting, preventing and treating influenza.

5 Claims, 15 Drawing Sheets

OTHER PUBLICATIONS

Pak, Charles C., "Detection of Influenza Hemagglutinin Interaction with Biological Membranes by Photosensitized Activation of [125I]Iodonaphthylazide", *Journal of Biological Chemistry*, 269(20), (May 20, 1994), 14614-14619.

Perlin, M., et al., "Photodynamic Inactivation of Influenza and Herpesviruses by Hematoporphyrin", *Antiviral Research*, vol. 7, No. 1, (1987), pp. 43-52.

Rai, S., et al., "Dramatic improvements in viral inastivation with brominated psoralens, naphthalenes and anthracenes", *Photochemistry and Photobiology*, 58(1), American Society for Photobiology, (1993), 59-65.

Raviv, Y, et al., "Quantitative Measurement of Fusion of HIV-1 and SIV with Cultured Cells Using Photosensitized Labeling", *Virology*, 293 (2), http://www.idealibrary.com, (Feb. 15, 2002), 243-251.

Raviv, Y., "Selective photoinduced uncoupling of the response of adenylate cyclase to gonadotropins by 5-iodonaphthyl 1-azide.", *Biochemistry*, 23(3) (1984), 503-508.

Raviv, Yosef, et al., "Detection of nearest neighbors to specific fluorescently tagged ligands in rod outer segment and lymphocyte plasma membranes by photosensitization of 5-iodonaphthyl 1-azide", *Biochemistry*, 28(3), (Feb. 7, 1989), 1313-1319.

Rossio, J. L, et al., "Inactivation of human immunodeficiency virus type 1 infectivity with preservation of conformational and functional integrity of virion surface proteins", *J Virol.*, 72(10), (Oct. 1998), 7992-8001.

Shao-Chieh, C., et al., "4-Alkylamino-3-Bromo-N-Alkyl-1,8-Naphthalimides; New Photochemically Activatble Antiviral Compounds", *Bioorganic & Medicinal Chemistry Letters*, 3(4), (1993), 555-556.

Snipes, et al., "Inactivation of Lipid-Containing Viruses By Hydrophobic Photosensitizers and Near-Ultraviolet Radiation", *photochemistry and Photobiology*, Oxford, vol. 29, No. 4, (Jan. 1, 1979), pp. 785-790.

Vzorov, A. N, et al., "Inactivation of human immunodeficiency virus type 1 by porphyrins", *Antimicrob Agents Chemother.*, 46(12), (Dec. 2002), 3917-25.

Wallis, C., et al., "Influenza Vaccine Prepared by Photodynamic Inactivation of Virus", *Journal of Immunology*, vol. 91, (Nov. 1963), pp. 677-682.

* cited by examiner

* = NOT PHOTOACTIVATED

LIVE EBOV | INA-INACTIVATED EBOV

□ PROTEIN CD4
▨ LIPID DIO

SEQUENCE LISTING

<160> NUMBER OF SEQ ID NOS: 9

<210> SEQ ID NO 1
<211> LENGTH: 15
<212> TYPE: PRT
<213> ORGANISM: Lassa virus

<400> SEQUENCE: 1

Arg Pro Leu Ser Ala Gly Val Tyr Met Gly Asn Leu Ser Ser Gln
1               5                   10                  15

<210> SEQ ID NO 2
<211> LENGTH: 15
<212> TYPE: PRT
<213> ORGANISM: Ebola virus

<400> SEQUENCE: 2

Trp Ile Pro Tyr Phe Gly Pro Ala Ala Glu Gly Ile Tyr Thr Glu
1               5                   10                  15

<210> SEQ ID NO 3
<211> LENGTH: 11
<212> TYPE: PRT
<213> ORGANISM: Ebola virus

<400> SEQUENCE: 3

Val Tyr Gln Val Asn Asn Leu Glu Glu Ile Cys
1               5                   10

<210> SEQ ID NO 4
<211> LENGTH: 9
<212> TYPE: PRT
<213> ORGANISM: Ebola virus

<400> SEQUENCE: 4

Asp Ala Val Leu Tyr Tyr His Met Met
1               5

<210> SEQ ID NO 5
<211> LENGTH: 8
<212> TYPE: PRT
<213> ORGANISM: Ebola virus

<400> SEQUENCE: 5

Arg Asn Ile Met Tyr Asp His Leu
1               5

<210> SEQ ID NO 6
<211> LENGTH: 16
<212> TYPE: PRT
<213> ORGANISM: Ebola virus

<400> SEQUENCE: 6

Leu Arg Ile Gly Asn Gln Ala Phe Leu Gln Glu Phe Val Leu Pro Pro
1               5                   10                  15

<210> SEQ ID NO 7
<211> LENGTH: 9
<212> TYPE: PRT
<213> ORGANISM: Ebola virus

<400> SEQUENCE: 7

Ser Phe Lys Ala Ala Leu Ser Ser Leu
1               5

```
<210> SEQ ID NO 8
<211> LENGTH: 9
<212> TYPE: PRT
<213> ORGANISM: Ebola virus

<400> SEQUENCE: 8

Pro Gly Pro Ala Lys Phe Ser Leu Leu
1               5

<210> SEQ ID NO 9
<211> LENGTH: 16
<212> TYPE: PRT
<213> ORGANISM: Ebola virus

<400> SEQUENCE: 9

Val Ser Thr Gly Thr Gly Pro Gly Ala Gly Asp Phe Ala Phe His Lys
1               5                   10                  15
```

INACTIVATED INFLUENZA VIRUS COMPOSITIONS

This application is a U.S. national stage filing from International Application No. PCT/US2007/007338 filed Mar. 23, 2007 and published as WO 2008/054481 on May 8, 2008, which claims priority to U.S. Provisional Application Ser. No. 60/785,781 filed Mar. 24, 2006, the contents of which are specifically incorporated herein their entirety. This application is also a continuation-in-part of co-pending U.S. patent application Ser. No. 11/525,250 filed Sep. 21, 2006, which is a U.S. national stage filing from International Application No. PCT/US2005/009559 filed Mar. 22, 2005 and published as WO 2005/093049 on Oct. 6, 2005, which claims priority to U.S. Provisional Application Ser. No. 60/555,268, filed Mar. 22, 2004; the contents of which applications and publications are also specifically incorporated herein in their entireties.

GOVERNMENT FUNDING

The invention described herein was developed with support from the National Cancer Institute. The United States Government may have certain rights in the invention.

SEQUENCE LISTING

The instant application contains a Sequence Listing which has been submitted in ASCII format via EFS-Web and is hereby incorporated by reference in its entirety. Said ASCII copy, created on May 25, 2012, is Sequence_Listing_CRF_NIHC6029 and is 1,930 bytes in size.

FIELD OF THE INVENTION

The invention is related to a method for universal inactivation of viruses, parasites and tumor cells. These inactivated agents can be used as vaccines against the diseases caused by such viruses, parasites and tumor cells. The inventive inactivation method preserves the integrity of structural and conformational features of the agent. Hence, the immunogenicity of the agent as a whole is maintained and can be safely used for vaccination without the threat of infection.

BACKGROUND OF THE INVENTION

Vaccination against pathogens has been one of the major accomplishments of medicine over the past century. While effective vaccines have been developed for a large number of diseases, development of safe and effective vaccines for a number of other diseases remains problematic. For example, the most commonly used approach for inactivation of enveloped viruses is cross-linking of surface glycoproteins by formaldehyde. While this approach results in inactivation of the enveloped viruses, covalent cross-linking of the surface proteins can severely distort the structure of immunogenic epitopes (Koch et al., Apmis 104:115-25 (1996)). The use of inactivated or killed microbial agents as a vaccine, although generally safe, will not always be effective if the immunogenic characteristics of the agent are altered. Indeed, the preferential degradation of certain antigens on the inactivated microorganisms might produce a weak or poorly targeted immune response that permits a pathological response when the host is later challenged with the live microorganism. On the other hand, while the preparation of live attenuated microbial agents as vaccines will often provide improved immunologic reactivity, use of such live attenuated microbial agents has an increased risk that the vaccine itself will be infectious. Such live attenuated vaccines can be infectious, for example, as a result of reversion, or the organism may be able to propagate and provide a reservoir for future infection.

Thus, one must generally choose between improved effectiveness and greater degree of safety when selecting between the viral inactivation and viral attenuation techniques for vaccine preparation. The choice is particularly difficult when the virus is resistant to inactivation and requires highly rigorous inactivation conditions that are likely to degrade the antigenic characteristics.

It is therefore desirable to provide improved methods for inactivating agents such as viruses, bacteria, cancer cells and other cell types, where the methods are capable of inactivating these agents without causing substantial degradation of the antigenic structure of the agents. In particular, the inactivated agents should be useful as vaccines and free from adverse side effects at the time of administration as well as upon subsequent challenge with the live agent.

SUMMARY OF THE INVENTION

The invention provides methods for inactivating an infective agent or cancer cell that involve exposing the agent or cell to a hydrophobic photoactivatable compound, for example, 1,5-iodonaphthylazide (INA). These photoactivatable compounds are non-toxic, hydrophobic compounds that penetrate into the innermost regions of biological membrane bilayers and selectively accumulate in such inner membrane regions. Upon irradiation with light, a reactive derivative of the compound is generated that binds to membrane proteins deep in the lipid bilayer. This process specifically inactivates integral membrane proteins embedded in the membrane while maintaining the structural integrity and activity of the proteins that protrude from the extracellular surface of the membrane. Such inactivation is so successful that the inactivated virus, microbe, infective agent, cancer cell or other agent of interest, is non-infective and can be used as a vaccine. In some embodiments, the agent is an inactivated virus, for example, influenza virus.

One aspect of the invention is a composition comprising a pharmaceutically acceptable carrier and an inactivated influenza virus, wherein the inactivated influenza virus is made by (a) contacting an influenza virus with an effective amount of a photoactivatable hydrophobic compound to form a mixture of the influenza virus with the photoactivatable hydrophobic compound, and (b) exposing the mixture to light for a time sufficient to generate the inactivated influenza virus.

The photoactivatable hydrophobic compound employed in the present compositions and methods is a compound of formula (I):

$$X\text{—}Ar\text{—}Y \qquad\qquad I$$

wherein:
Ar is a hydrophobic moiety; and
X and Y are each independently hydrogen or a reactive group,
provided that at least one of X or Y is a reactive group.
The Ar group is a moiety that preferentially partitions out of an aqueous environment and into a cellular or viral membrane. In another embodiment, the Ar group is a linear, branched, cyclic or acyclic hydrocarbon or a combination thereof. In another embodiment, the Ar group is a fatty acid, alkyl, adamantane, phenyl, naphthyl, anthracene, pyrene, or phenanthracene group.

The X and Y reactive groups separately are azido, halo, halo lower alkyl, diazirene, azidocarbonyl)oxy, haloacetamide, amine, maleimide, isocyanato, isothiocyanato, acyl halide, succinimidyl ester, or sulfosuccinimidyl ester.

Examples of photoactivatable hydrophobic compounds that can be used in the invention include azidobenzene, 1-azidonaphthalene, 4-azido-2-nitro-1-(phenylthio)benzene, 1-azido-4-iodobenzene, 1-azido-5-iodonaphthalene, 3-phenyl-3H-diazirene, 3-phenyl-3-(trifluoromethyl)-3H-diazirene, 3-(3-iodophenyl)-3-(trifluoromethyl)-3H-diazirene, 1-azidopyrene, adamantanediazirene, 12-(4-azido-2-nitrophenoxy)-stearic acid, w-(m-diazirinophenoxy)fatty acid, 12-[(azidocarbonyl)oxy]stearic acid, 12-azidostearic acid, 11-(3-azidophenoxy)undecanoic acid or w-(m-diazirinophenoxy)undecanoic acid. In some embodiments, the photoactivatable hydrophobic compound is 1,5-iodonaphthyl azide.

The light employed can be ultraviolet light. In other embodiments, the light is visible light and an effective amount of a photosensitizer chromophore is included in the mixture. Examples of photosensitizer chromophores that can be used include porphyrin, chlorin, bacteriochlorin, purpurin, phthalocyanine, naphthalocyanine, merocyanines, carbocyanine, texaphyrin, or non-tetrapyrrole chromphores. Further examples include the photosensitizer chromophore is fluorescein, eosin, bodipy, nitro-benzo-diazol (NBD), erythrosine, acridine orange, doxorubicin, rhodamine 123, or picoerythrin.

A variety of viruses can be inactivated and used in the compositions of the invention. One example of a virus that can be inactivated and used in the compositions and methods of the invention is an influenza virus. The influenza virus can be an influenza virus type A, influenza virus type B or any other type of influenza virus. Further examples of viruses that can be inactivated by use of the inventive methods include a hepatitis A virus, hepatitis B virus, hepatitis C virus, simian immunodeficiency virus, human immunodeficiency virus, Ebola virus, poxvirus, herpes virus, adenovirus, papovavirus, parvovirus, reovirus, orbivirus, picornavirus, rotavirus, alphavirus, rubivirus, influenza virus type A, influenza virus type B, flavivirus, coronavirus, paramyxovirus, morbillivirus, pneumovirus, rhabdovirus, lyssavirus, orthmyxovirus, bunyavirus, phlebovirus, nairovirus, hepadnavirus, arenavirus, retrovirus, enterovirus, rhinovirus, filovirus, hemorrhagic fever virus, Chikungunya virus, Japanese encephalitis virus, Monkey pox virus, variola virus, Congo-Crimean hemorrhagic fever virus, Junin virus, Omsk hemorrhagic fever virus, Venezuelan equine encephalitis virus, Dengue fever virus, Lassa fever virus, Rift valley fever virus, Western equine encephalitis virus, Eastern equine encephalitis virus, Lymphocytic choriomeningitis virus, Russian Spring-Summer encephalitis virus, White pox, Machupo virus, Smallpox virus, Yellow fever virus, Hantaan virus, Marburg virus, or Tick-borne encephalitis virus. In some embodiments, the virus is an enveloped virus.

Another aspect of the invention is a vaccine comprising the any of the inactivated viral, bacterial, fungal, cellular or parasite compositions of the invention. In one embodiment the vaccine comprises an inactivated influenza virus.

Another aspect of the invention is a method of inactivating a virus, for example, an influenza virus, comprising contacting the virus with an effective amount of a photoactivatable hydrophobic compound to form a mixture of the virus and the photoactivatable hydrophobic compound, and exposing the mixture to light for a time sufficient to inactivate the virus. In some embodiments the light is ultraviolet light. In other embodiments, the light is visible light and an effective amount of a photosensitizer chromophore is included in the mixture.

Another aspect of the invention is a method of inactivating an influenza virus comprising contacting the influenza virus with an effective amount of 1,5-iodonaphthyl azide to form a mixture of the influenza virus and the 1,5-iodonaphthyl azide, and exposing the mixture to ultraviolet light for a time sufficient to inactivate the influenza virus.

As described herein, while treatment with the hydrophobic photoactivatable compound (e.g., 1,5-iodonaphthylazide (INA)) produces non-infective virus compositions, the structural elements needed for generating a strong immune response against the virus are preserved. Thus, for example, influenza virus treated with INA still exhibits hemagglutinin and/or neuraminidase activity. Moreover, while INA-treated influenza viruses can still bind to mammalian cells, these viruses cannot fuse with the cells and therefore cannot initiate an infective cycle.

DESCRIPTION OF THE FIGURES

FIG. 11A-B illustrate that treatment with INA does not change Ebola virus morphology or the immunoreactivity of Ebola surface glycoprotein (EBOV GP). FIG. 11A shows electron microscopic images of live (images on the left) and INA-inactivated (images on the right) mouse adapted EBOV. Top two panels: Negative staining. Lower four panels: Immunostaining with an anti-GP mAb specific for a conformational epitope. FIG. 11B shows results of a viral capture assay with live (top panel) and INA-inactivated (bottom panel) EBOV. Mouse monoclonal antibodies against EBOV GP (6D3, 13C6-1-1-1, 8C10-1-1, 3H8-1-1, 3H5-1-1, 4D4-1-1, 1H7-1-1, and 6D8), or control anti-Myc or anti VP40 (AE11) mAb were immobilized on 96 well plates, and incubated with live (top panel) or INA-inactivated (bottom panel) EBOV. Captured virus was quantified by a real time PCR assay.

FIG. 12 illustrates that the anti-Ebola serum titer of mice vaccinated with INA-inactivated EBOV was much greater than that of control mice (who received no INA-inactivated EBOV) and somewhat greater than mice who received only one injection of INA-inactivated EBOV. Sera from control and vaccinated mice were serially diluted in PBS and tested in an ELISA to measure antibody titer by end point dilution. The dilution at which the optical density (OD) reached the background (0.2) is presented for each mouse. Each symbol represents one mouse. The mean titer for each group is shown as (-).

FIG. 13A-B shows that vaccination with INA-inactivated EBOV protects mice against lethal EBOV infection. FIG. 13A shows the survival of groups of 8-10 mice that were vaccinated once (one vaccine) or twice (two vaccines) with INA-inactivated EBOV and challenged with live EBOV (1000 Pfu) three weeks later. Another two groups of ten mice were immunized once with INA-inactivated EBOV (short term) or PBS and challenged three days later with 1000 Pfu EBOV. Survival was monitored for 20 days. All vaccinated animals exhibited high levels of survival. FIG. 13B shows the post-challenge anti-Ebola titers of mice from the challenge experiment described for FIG. 13A. Antibody titers were measured against whole viral antigen using ELISA.

FIG. 15A shows the results for untreated virus. FIG. 15B shows the results for influenza virus treated with 100 μM INA. The blue lines represent pH 7.4 virus (no fusion). The green lines show data for dequenching induced by a virus that was pre-exposed to pH. 5.0 at 4° C. and incubated with cells at pH 7.4. The red lines show data for dequenching induced by a virus that was pre-exposed to pH. 5.0 at 37° C. and incubated with cells at pH 7.4.

DETAILED DESCRIPTION OF THE INVENTION

Figure 1:
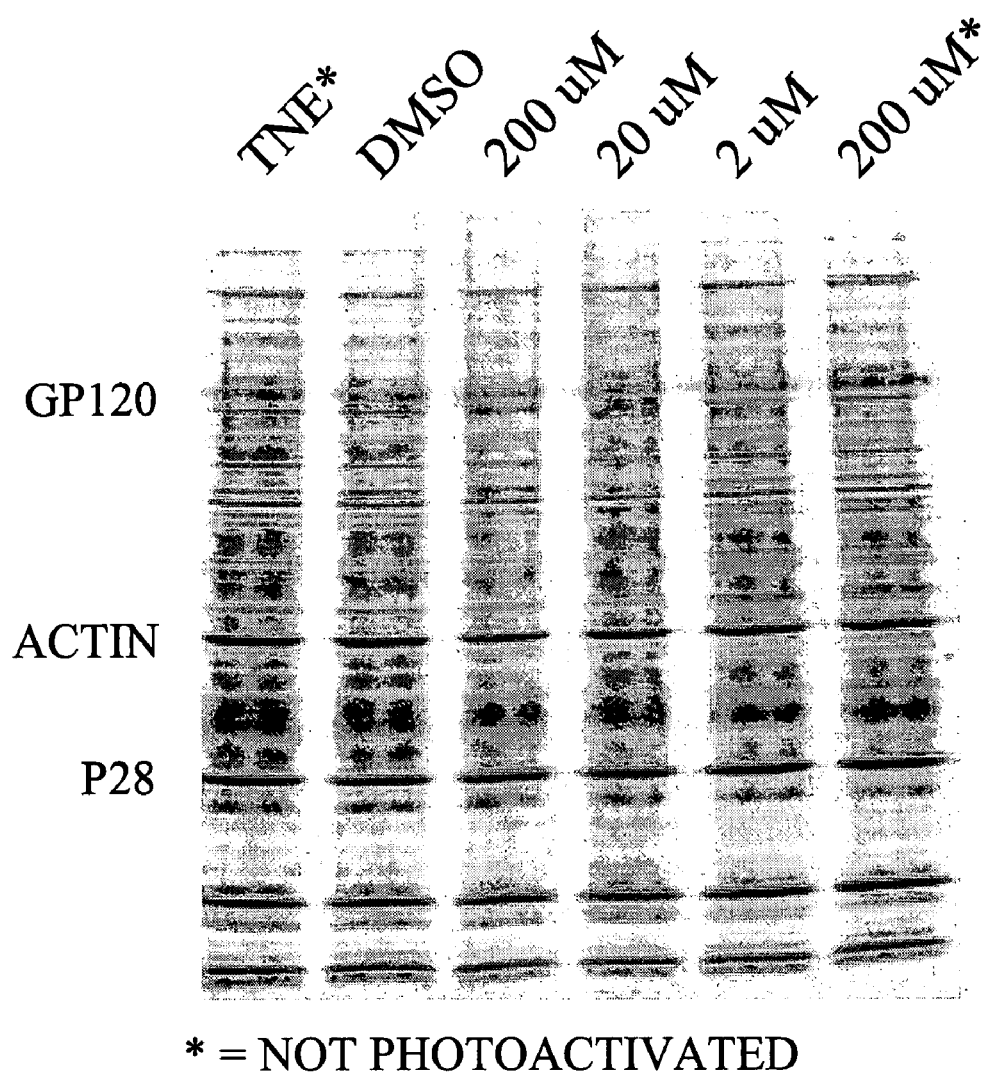
FIG. 1 illustrates that the integrity of SIV proteins was substantially unaffected by INA treatment. The integrity of the SIV virus after the INA treatment was evaluated by recovery of the virus in the pellet using standard procedures for centrifugation of virus and by identifying whether the molecular weights of major viral proteins in the pellet changed upon INA treatment as detected by SDS-PAGE. Similar results were obtained with INA treated HIV (not shown).

According to the invention, treatment of influenza virus with a photoactivatable hydrophobic compound of the invention blocks viral infectivity and fusion of influenza virus with mammalian cells. Moreover, administration of influenza virus treated with such a photoactivatable hydrophobic compound protects mammals against the effects of subsequent influenza viral infections, even if the mammal becomes infected or exposed to a different strain or type of influenza virus. Thus, the invention provides immunological compositions and vaccines that contain influenza virus with a photoactivatable hydrophobic compound of the invention.

Similarly, treatment of tumor cells with a photoactivatable hydrophobic compound of the invention blocks tumor cell division and tumor cell colony formation with substantially no detectable damage to the structural integrity of the tumor cells. Moreover, when live HIV, SIV and Ebola viral particles are treated with appropriate concentration of such photoactivatable hydrophobic compounds, substantially no infectivity is observed. Minor, generally insubstantial changes in the structural integrity of virus particles were observed. These modified viral particles reacted with monoclonal antibodies directed against selected viral proteins and the inactivated viruses bound to their target cells. However, viral fusion with the membrane was impaired by use of the present inventive methods.

Hence, the invention provides new methods for inactivating viruses, bacteria, parasites and tumor cells. These inactivated agents can be used in compositions to stimulate an immune response against active viruses, bacteria, parasites and tumor cells. In another embodiment, the invention provides vaccines to prevent the diseases caused by such viruses, bacteria, parasites and tumor cells.

Photoactivatable Hydrophobic Compounds

Accordingly, as provided herein, a photoactivatable hydrophobic compound of the following formula (I) can be used to inactivate viruses, parasites and tumor cells.

$$X-Ar-Y \quad \text{I}$$

wherein:

Ar is a hydrophobic moiety; and

X and Y are each independently hydrogen or a reactive group, provided that at least one of X or Y is a reactive group.

The Ar hydrophobic moiety can be any moiety that preferentially partitions out of an aqueous environment and into a cellular or viral membrane. Examples of Ar hydrophobic moieties include linear, branched, cyclic and acyclic hydrocarbons and combinations thereof. The cyclic groups employed can be non-aromatic or aromatic ring moieties. For example, the Ar hydrophobic moiety can be a fatty acid, alkyl, adamantane, phenyl, naphthyl, anthracene, pyrene, phenanthracene or similar moiety.

The X and Y reactive groups are functional groups that are chemically reactive (or that can be made or activated to be chemically reactive) with functional groups typically found in biological materials, or with functional groups that can be readily converted to chemically reactive groups using methods well known in the art. In one embodiment of the invention, the X and/or Y reactive groups are separately azido ($-N_3$), halo (Cl, Br or I), halo lower alkyl (e.g. $CF_3$), diazirene, azidocarbonyl)oxy ($-O-CO-N_3$), haloacetamide ($-NH-(C=O)-CH_2-Z$), where Z is Cl, Br or I. Alternatively, the reactive groups are separately amine, maleimide, isocyanato ($-N=C=O$), isothiocyanato ($-N=C=S$), acyl halide, succinimidyl ester, or sulfosuccinimidyl ester. In another embodiment, the reactive groups are carboxylic acid (COOH), or derivatives of a carboxylic acid. An appropriate derivative of a carboxylic acid includes an alkali or alkaline earth metal salt of carboxylic acid. Alternatively, the reactive groups are reactive derivatives of a carboxylic acid ($-COOR$), where the reactive group R is one that activates the carbonyl group of $-COOR$ toward nucleophilic displacement. In particular, R is any group that activates the carbonyl towards nucleophilic displacement without being incorporated into the final displacement product. Examples of COOR groups include esters of phenol or naphthol that are further substituted by at least one strong electron withdrawing group, or a carboxylic acid activated by carbodiimide. In some embodiments the X and Y reactive groups are acyl chlorides, or azido, succinimidyl or sulfosuccinimidyl esters. Additional charged groups include, among others, sulfonyl halides, sulfonyl azides, alcohols, thiols, semicarbazides, hydrazines or hydroxylamines.

Examples of photoactivatable hydrophobic compounds that can be used in the invention include the following compounds:

azidobenzene   1-azidonaphthalene 4-azido-2-nitro-1-(phenylthio)benzene   1-azido-4-iodobenzene 1-azido-5-iodonaphthalene   3-phenyl-3H-diazirene 3-phenyl-3-(trifluoromethyl)-3H-diazirene   3-(3-iodophenyl-3-(trifluoromethyl)-3H-diazirene 1-azidopyrene   adamantanediazirene

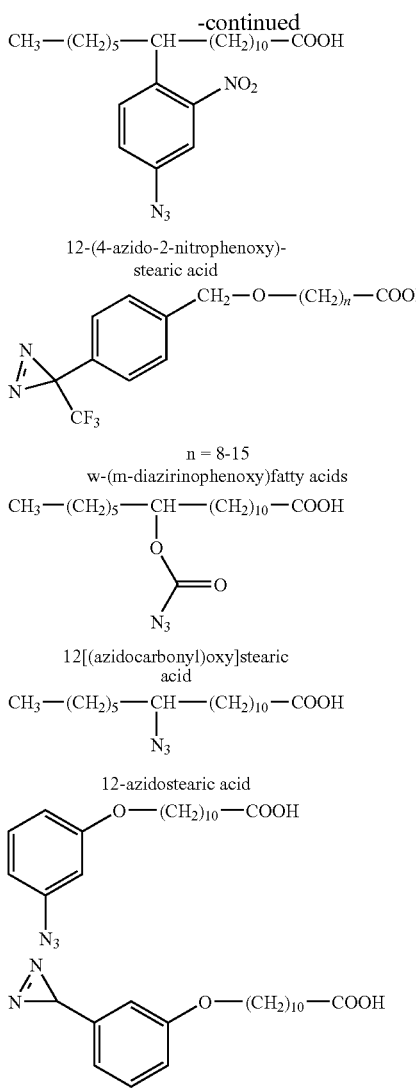

12-(4-azido-2-nitrophenoxy)-stearic acid n = 8-15
w-(m-diazirinophenoxy)fatty acids 12[(azidocarbonyl)oxy]stearic acid 12-azidostearic acid 11-(3-azidophenoxy)undecanoic acid  w-(m-diazirinophenoxy)undecanoic acid In one embodiment, 1,5-iodonaphthyl azide (INA) is employed as a photoactivatable hydrophobic compound. INA is a non toxic hydrophobic compound. The structure for 1,5-iodonaphthyl azide (INA) is provided below. See also, Bercovici and Gitler 1978, Biochemistry, 17: 1484-89.

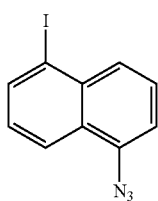

Upon exposure to cells, photoactivatable hydrophobic compounds of the invention will penetrate into the innermost regions of biological membrane bilayers and will accumulate selectively in these regions. Photoactivatable hydrophobic compounds of the invention are also light sensitive. Upon irradiation with ultraviolet light (e.g. 320 to 400 nm) a reactive derivative is generated that binds to membrane proteins deep in the lipid bilayer. This process specifically inactivates integral membrane proteins embedded in the membrane while maintaining the integrity and activity of the proteins that protrude from the extracellular surface of the membrane.

In another embodiment, the photoactivatable hydrophobic compounds of the invention can be used for inactivation of viruses, bacteria, parasites and tumor cells using visible light. However, when visible light is used a photosensitizer chromophore is needed. This photosensitizer chromophore has an absorption maximum in the visible light range and can photosensitize the photoactivatable hydrophobic compounds of the invention. In general, the photosensitizer chromophore have absorption maxima in the range of about 450 to about 525 nm or about 600 to about 700 nm. The photosensitizer chromophore can be a porphyrin, chlorin, bacteriochlorin, purpurin, phthalocyanine, naphthalocyanine, merocyanines, carbocyanine, texaphyrin, non-tetrapyrrole, or other photosensitizer known to one of skill in the art. Specific examples of photosensitizer chromophores include fluorescein, eosin, bodipy, nitro-benzo-diazol (NBD), erythrosine, acridine orange, doxorubicin, rhodamine 123, picoerythrin and the like.

Treatment with Photoactivatable Hydrophobic Compounds

As provided herein, viruses, bacteria, parasites and tumor cells can be inactivated by exposure to photoactivatable hydrophobic compounds. In some embodiments the photoactivatable hydrophobic compound is 1,5-iodonaphthyl azide (INA) or a related compound. After contacting the photoactivatable hydrophobic compound with the virus, parasite or tumor cell to form a mixture thereof, the mixture is exposed to light. If the virus, parasite or tumor cell is contacted with just the photoactivatable hydrophobic compound, ultraviolet light is used. If the virus, parasite or tumor cell is contacted with both the photoactivatable hydrophobic compound and a photosensitizer chromophore that absorbs visible light, then visible light can be used instead. Exposure to ultraviolet light directly photoactivates the photoactivatable hydrophobic compound within viral and cellular membranes. Exposure to visible light first photoactivates the photosensitizer chromophore, which then activates or photosensitizes the photoactivatable hydrophobic compound within viral or cellular membranes. In either case, a reactive derivative of the photoactivatable hydrophobic compound is generated that binds to membrane proteins deep within the lipid bilayer. This process causes specific inactivation of integral membrane proteins embedded in the membrane, while maintaining the integrity and activity of proteins that protrude outside of the membrane.

Prior to exposure to a photoactivatable hydrophobic compound, the viruses, parasites or tumor cells can be washed to remove media, waste and other materials that might reduce partitioning of the photoactivatable hydrophobic compound into viral or cellular membranes. For example, the viruses, parasites or tumor cells can be washed in serum-free media, phosphate-buffered saline or other solutions selected by one of skill in the art.

The amount of photoactivatable hydrophobic compound used to inactivate a virus, bacteria, parasite or tumor cell can vary and may depend upon the type of virus, bacteria, parasite or tumor cell as well as the conditions under which the photoactivatable hydrophobic compound is reacted with the virus, bacteria, parasite or tumor cell. For example, if competing hydrophobic molecules are present in the media, then larger amounts of the photoactivatable hydrophobic compound may be needed.

In some embodiments, the concentration of photoactivatable hydrophobic compound employed in a mixture with a virus, parasite or tumor can vary from about 0.1 micromolar to about 1 millimolar, or from about 1 micromolar to about 700 micromolar, or from about 10 micromolar to about 500 micromolar, or from about 20 micromolar to about 400 micromolar, or from about 50 micromolar to about 300 micromolar, or from about 100 micromolar to about 250 micromolar.

When expressed as a ratio of the amount of photoactivatable hydrophobic compound employed per amount of viral, parasite or tumor protein, this ratio can vary from about 0.1 micrograms photoactivatable hydrophobic compound per milligram of viral, parasite or tumor protein to about 500 micrograms photoactivatable hydrophobic compound per milligram of viral, parasite or tumor protein. In other embodiments, the amount of photoactivatable hydrophobic compound used can vary from about 0.5 to about 200, or about 1 to about 150, or about 2 to about 125, or about 3 to about 100 micrograms photoactivatable hydrophobic compound per milligram of viral, parasite or tumor protein.

The amount of photosensitizer chromophore used to activate the photoactivatable hydrophobic compound can also vary and depends to some extent on the photosensitizer chromophore used, the photoactivatable hydrophobic compound employed and the type of virus, bacteria, parasite or tumor cell. For example, about 0.01 mg/ml to about 50 mg/ml photosensitizer chromophore can be used, or about 0.1 mg/ml to about 5 mg/ml photosensitizer chromophore can be used, or about 0.3 mg/ml to about 1 mg/ml photosensitizer chromophore can be used.

After forming a mixture of the virus, bacteria, parasite or tumor cell with a photoactivatable hydrophobic compound, the mixture is exposed to light for a time and under conditions sufficient for generating a reactive hydrophobic derivative that can bind to membrane proteins within the lipid bilayer. The ultraviolet light employed when only the photoactivatable hydrophobic compound is present has a wavelength that is generally above that absorbed by proteins and nucleic acids. Such a wavelength of ultraviolet light does not cause substantial damage to such proteins and nucleic acids. Thus, for example, the wavelength can be about 320 nm to about 400 nm. In some embodiments, the wavelength is about 330 nm to about 380 nm. In other embodiments, the wavelength is about 340 nm to about 360 nm.

Visible light of an appropriate wavelength can be used when a photosensitizer chromophore is employed that is incubated with or is localized in the vicinity of the hydrophobic photoactivatable compound. In general, the photosensitizer chromophores have absorption maxima in the range of about 450 to about 525 nm or about 600 to about 700 nm.

Light for photoactivation of the photosensitizer chromophore or the hydrophobic derivative can be from various light sources. For example, suitable light sources include broadband conventional light sources, broad arrays of LEDs, laser beams, defocused laser beams, optical fiber devices and transillumination. The light can be filtered to eliminate certain types or wavelengths of light. Hence, the light can be filtered to provide ultraviolet light (e.g. 320 to 400 nm), or visible light of selected wavelengths (e.g., 450 to 525 nm or 600 to 700 nm). The light can also be filtered to reduce heat production, for example, by passing the light through water.

Different light sources of different powers can be used: An incandescent light source like tungsten or halogen lamps will have a power range from 100-200 Watt. Mercury or Xenon light sources have a power range of about 100-1000 Watt. A laser source will have the power range of 1-10 Watts. When visible light is used in the presence of a photosensitizer chromophore, the tungsten, halogen, Mercury and Xenon light sources should be equipped with optical filters or a monochromator that will filter out all wavelengths below 400 nm. When a laser is used, the appropriate wavelength line of 400 nm or higher should be used depending on the photosensitizer chromophore employed. Regardless of the light source the intensities of light on the target sample should be in the range of 1-50 milliwatt/cm$^2$/min depending on the nature of the sample and the area irradiated.

Light exposure times can vary. For example, one of skill in the art may choose to expose a mixture of a photosensitizer chromophore and/or a photoactivatable hydrophobic compound with a virus, bacteria, parasite or tumor cell to a light source for about 1 second to about 20 minutes, or about 3 seconds to about 15 minutes, or about 5 seconds to about 10 minutes, or about 7 seconds to about 7 minutes, or about 30 seconds to about 5 minutes. A series of short (e.g. about 1 to about 60 seconds) or longer (e.g. about 20 to about 60 seconds) light exposures can also be employed. When a laser is used, substantially shorter exposure times are typically used, for example, about 0.1 second to about 5 seconds, or about 0.5 seconds to about 3 seconds.

As is appreciated by one of skill in the art, the exposure time can vary depending on the wattage of the light employed. Either cultures or plates of viruses, bacteria, parasites or tumor cells can be treated with a selected photoactivatable hydrophobic compound and/or a photosensitizer chromophore and then exposed to light. The exposure time and wattage of the light employed may be different if a culture or plate of viruses/cells is employed. For example, less exposure may be needed for plated viruses/cells than for viruses/cells cultured in suspension because the depth of the culture may influence the degree to which the light penetrates the culture. Hence, some variation and deviation from the ranges provided herein is possible without deviating from the scope of the invention.

As described in more detail herein, INA has been shown by the inventors to penetrate into the inner most segments of membrane bilayers and accumulate selectively in this domain. As shown herein, upon irradiation of the organism or cell with ultraviolet light (e.g., 320-400 nm), INA is photoactivated in the membrane to generate a reactive derivative that binds to membrane proteins deep within the lipid bilayer. This process causes specific inactivation of integral membrane proteins embedded in the membrane, while maintaining the integrity and activity of proteins that protrude outside the membrane (Raviv et al, 1984 Biochemistry, 23, 503-508).

Methods of Using the Inactivated Microbes, Parasites and Tumor Cells

The invention provides a method that can universally inactivate viruses, bacteria, parasites and tumor cells in a way that they can be safely used as immunological compositions or vaccines to inhibit the disease they cause. The inactivation kills the organism or cell in a specific manner that maintains it's structural and conformational. Hence, the structure of the inactivated virus/cell is similar to that of the live virus/cell. In this way, the immunogenicity of the organism or cell as a whole is maintained and can be safely used to stimulate the immune system of a subject animal or patient. Similarly, the inactivated viruses, bacteria, cancer cells or parasites of the invention can be used for vaccination without causing disease or other negative side effects.

A study conducted by the inventors showed that INA treatment of tumor cells blocked their ability to divide and form colonies, with no detectable damage to the structural integrity of the cells.

Figure 2:
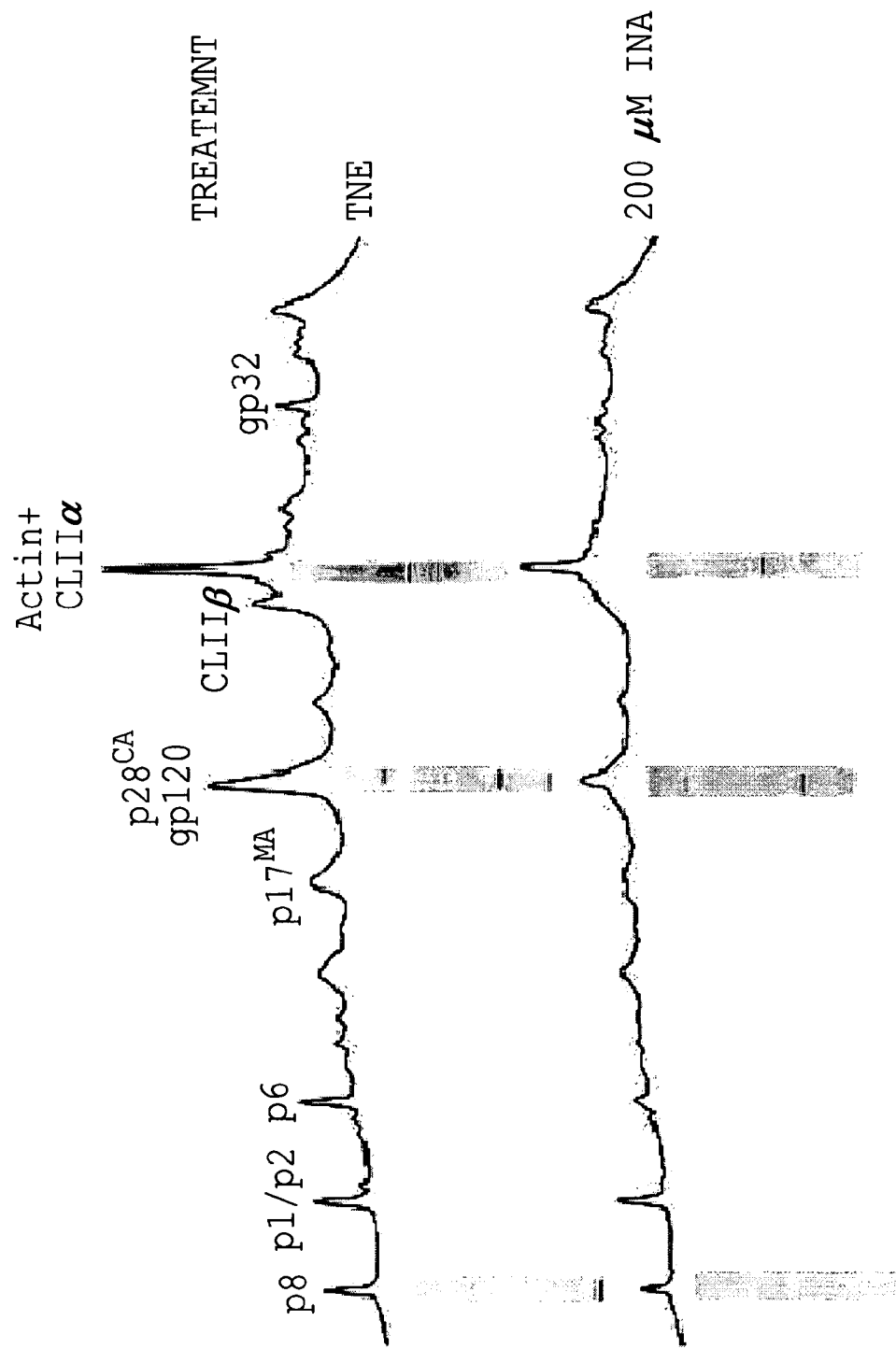
FIG. 2 shows that all detected viral proteins in INA-treated viruses were modified to some extent by INA as measured by their migration patterns on a reverse phase HPLC column. Hence, while the molecular masses of INA-treated viral proteins as observed by SDS-PAGE in FIG. 1 were not changed, some chemical modification of the viral proteins could be observed by HPLC analysis under reducing conditions.
Figure 3:
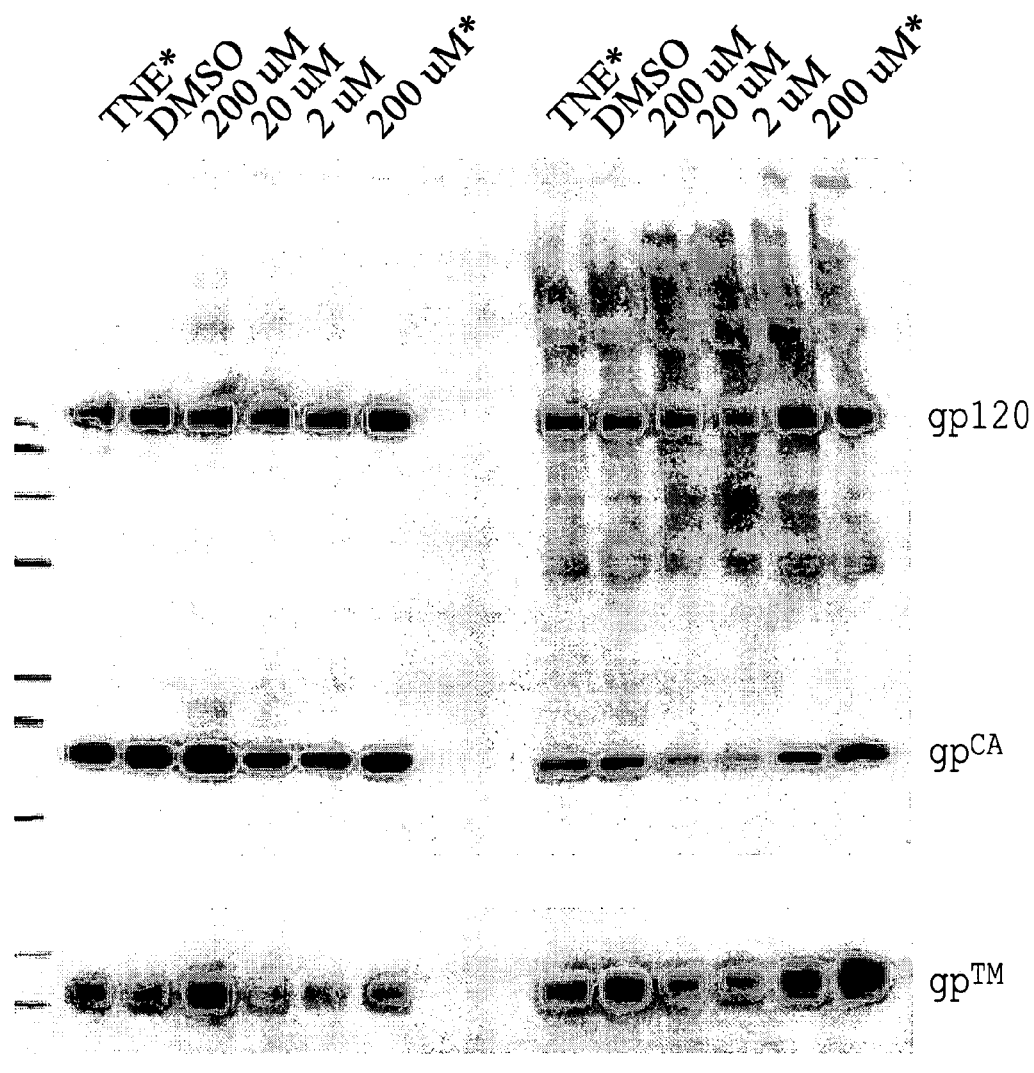
FIG. 3 shows that viral proteins from INA treated virus were still recognized by monoclonal antibodies as revealed by western blot analysis under reducing (R) and non-reducing (NR) conditions.
Figure 4:
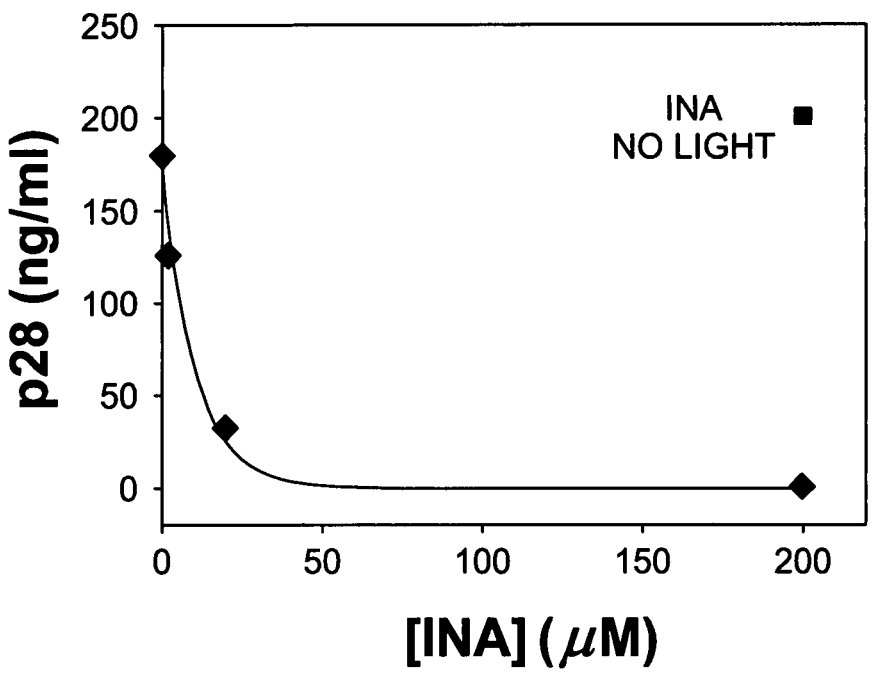
FIG. 4 illustrates dose-dependent inactivation of SIV infectivity by INA. AA2 cells were infected with SIV and treated with INA at the concentrations indicated (0.0 µM, 2 µM, 20 µM, and 200 µM). Infectivity was tested 11 days after infection by p28 determination as described in Example 1. The experiment was repeated three times with similar results.
Figure 5:
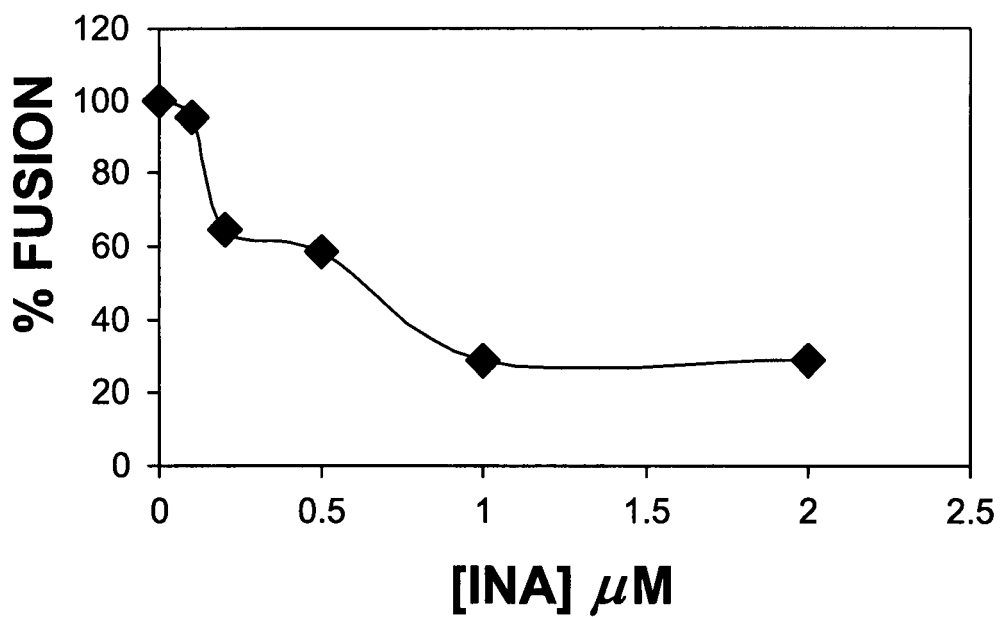
FIG. 5 illustrates that INA treatment blocks fusion of SIV with the target cell at the plasma membrane level, as measured by a photosensitized labeling method developed by the inventors. See Raviv et al. (2002) Virology, 293, 243-251.
Figure 6:
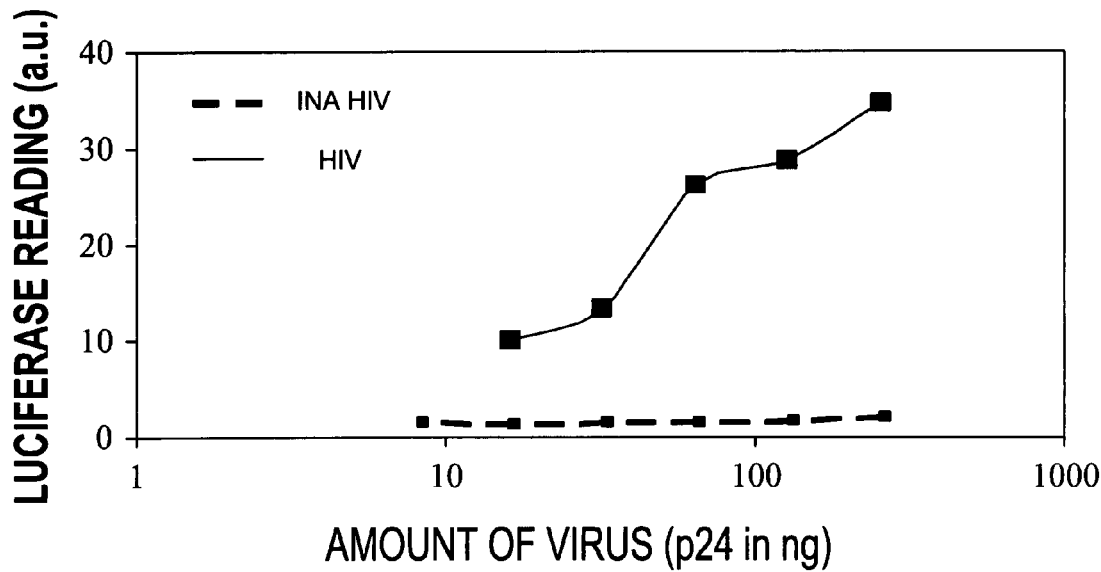
FIG. 6 illustrates the effect of INA treatment on HIV infectivity as measured by a luciferase reporter gene assay. As illustrated, INA-treated HIV exhibit essentially no transcription from viral promoters within the HIV LTR. These results further confirm that the INA-treated viruses used to generate the results in FIG. 1 were indeed inactivated.
Figure 7:
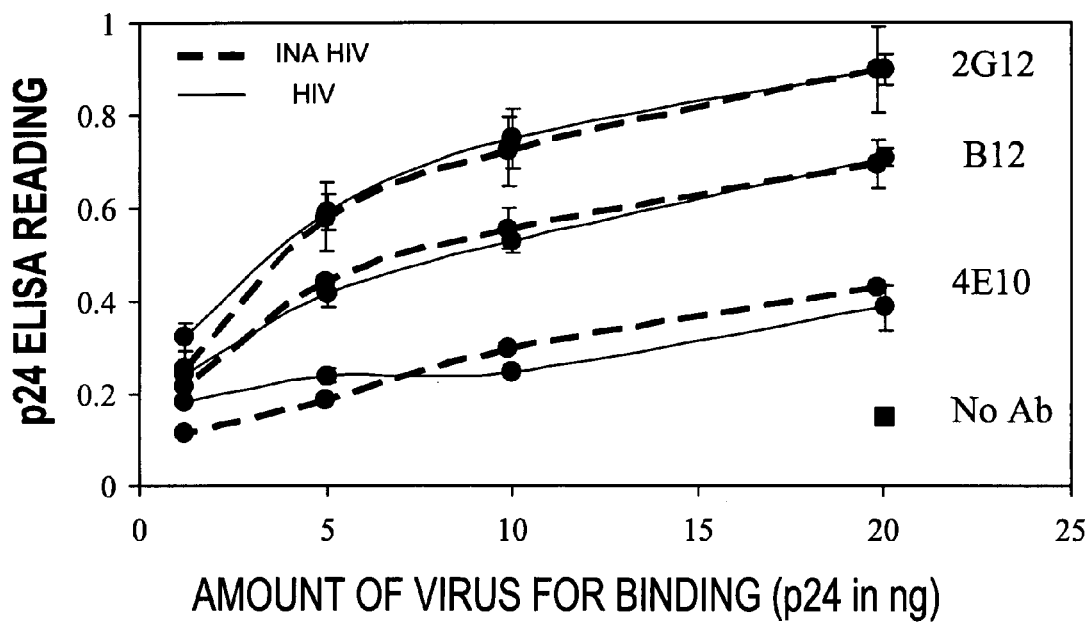
FIG. 7 illustrates that INA-treatment of HIV causes substantially no change in the epitopes recognized by three anti-HIV neutralizing antibody preparations. The antibody preparations tested were the 2G12, B12 and 4E10 antibody preparations. As shown, the amount of virus bound by the three antibody preparations did not change when HIV was treated with INA (dashed lines) as compared to untreated HIV (solid lines).

Studies by the inventors show that INA can also be used to inactivate live HIV, SIV and Ebola viruses. In particular, INA treatment produced inactive viruses with no detectable infectivity (Table 1 and FIG. 6) and with no significant change to their structural integrity (FIGS. 1, 3 and 4). Minor modifications to viral proteins were detected (FIG. 2). However, these modifications did not affect the ability of these proteins to react with antibodies that are known to bind to SIV or HIV (FIGS. 3 and 7). More significantly, viral infectivity was reduced to essentially zero by treatment of SIV with as little as 50 μM INA (FIG. 4). Moreover, the INA treatment impaired the ability of the virus to fuse with the target cell at the plasma membrane level (FIG. 5) and to express virally encoded functions (FIG. 6). Viral growth in cells that normally would become infected was essentially eliminated.

Hence, the INA treatment procedures of the invention generate inactive viruses that can be used in a manner similar to aldrithiol inactivated HIV (developed by the AIDS vaccine program SAIC). Alternatively, the INA-inactivation procedures of the invention can be used in conjunction with aldrithiol inactivation procedures to generate inactive HIV that comply with the requirements of the FDA. Thus, two mechanistically independent methods of inactivation can be used to provide a prophylactic AIDS or HIV vaccine.

The present invention is therefore directed to methods of treating or preventing or otherwise ameliorating microbial or parasitic infections in a mammal, as well as other animals, such as farm animals and birds. In another embodiment, the invention provides to methods of treating or preventing or otherwise ameliorating cancer in a mammal, as well as other animals, such as farm animals and birds. These methods include administering to the animal an effective amount, for example, a therapeutically effective amount of an inactivated agent of the present invention, wherein the agent may cause an infection or cancer when not inactivated as described herein.

Prevention or treatment of microbial infections, parasitic infections or cancer is intended to include the alleviation of or diminishment of at least one symptom typically associated with the infection or cancer. Prevention or treatment also includes alleviation or diminishment of more than one symptom. Ideally, treatment with the inactivated agents of the invention generates immunity in the animal towards the agent while prevention by the inactivated agents of the invention substantially eliminates the symptoms associated with the infection or cancer.

Microbial infections that can be treated by the present inactivated agents include infections by any target microbial organisms that can infect a mammal or other animal. Such target microbial organisms include essentially any virus, bacterium, fungus, single cell organism or parasite that can infect an animal, including mammals. For example, target microbial organisms include viruses, bacteria, fungi, yeast strains and other single cell organisms. In another embodiment, the inactivated agents of the invention can give rise to immunity against both gram-negative and gram-positive bacteria.

Treatment of, or prevention of, viral, bacterial, fungal, microbial or parasitic infections is intended to include the alleviation of or diminishment of at least one symptom typically associated with the infection. The treatment also includes alleviation or diminishment of more than one symptom. The treatment may cure the infection, e.g., it may substantially prevent the infection and/or eliminate the symptoms associated with the infection.

Exemplary viral infections that can be treated by the present inactivated agents include infections by any virus that can infect animals (including but not limited to mammals), including enveloped and non-enveloped viruses, DNA and RNA viruses, viroids, and prions. Hence, for example, infections or unwanted levels of the following viruses and viral types can be treated, prevented or addressed by the present inactivated agents: human immunodeficiency viruses (HIV), simian immunodeficiency viruses (SIV), Ebola viruses, hemorrhagic fever viruses, hepatitis A viruses, hepatitis B viruses, hepatitis C viruses, influenza viruses, poxviruses, herpes viruses, adenoviruses, papovaviruses, parvoviruses, reoviruses, orbiviruses, picornaviruses, rotaviruses, alphaviruses, rubiviruses, influenza virus type A and B, flaviviruses, coronaviruses, paramyxoviruses, morbilliviruses, pneumoviruses, rhabdoviruses, lyssaviruses, orthmyxoviruses, bunyaviruses, phleboviruses, nairoviruses, hepadnaviruses, arenaviruses, retroviruses, enteroviruses, rhinoviruses and the filoviruses.

In some embodiments, the viruses are influenza or filoviruses. Filoviruses are viruses belonging to the family Filoviridae, which is in the order Mononegavirales. These viruses are single stranded negative sense RNA viruses that target primates. There are two general viruses, the Ebola virus (Ebolavirus, with four species) and the Marburg virus (Marburgvirus). These viruses cause horrific viral hemorrhagic fevers, characterized by massive bleeding from every orifice of the body. Ebola destroys the immune system in an explosive manner. Marburg virus typically has a mortality rate of at least 25%, while Ebola virus, depending on the species, has a mortality rate of anywhere from 50% to 90%. The virus is spread through bodily fluids. They are classified by the Centers for Disease Control and Prevention as Biosafety Level 4. This means that they are among the most lethal and destructive viruses known to man. The filovirus viral particles are characteristically shaped as long, cylindrical, filamentous particles which may be straight, curved, coiled, or found in a "6" or "U" shaped configuration. They are occasionally branched and the particles vary greatly in length but the diameter (about 80 nm) is consistently observed. The filovirus virions are produced by budding from an infected cell, and consist of the viral RNA strand and proteins encapsulated in a lipid membrane formed from the host cell's plasma membrane.

Infections or unwanted levels of the following target viruses and viral types that are believed to have potential as biological weapons can be treated, prevented or addressed by the present inactivated agents: hemorrhagic fever viruses (HFVs), Filoviruses, Chikungunya virus, Japanese encephalitis virus, Monkey pox virus, variola virus, Congo-Crimean hemorrhagic fever virus, Junin virus, Omsk hemorrhagic fever virus, Venezuelan equine encephalitis virus, Dengue fever virus, Lassa fever virus, Rift valley fever virus, Western equine encephalitis virus, Eastern equine encephalitis virus, Lymphocytic choriomeningitis virus, Russian Spring-Summer encephalitis virus, White pox, Ebola virus, Machupo virus, Smallpox virus, Yellow fever virus, Hantaan virus, Marburg virus, and Tick-borne encephalitis virus.

Similarly, infections or unwanted levels of the following examples of target microbial organisms can be treated, prevented or addressed by the present inactivated agents: *Aeromonas* spp. (including, for example, *Aeromonas hydrophila*, *Aeromonas caviae* and *Aeromonas sobria*), *Bacillus* spp. (including, for example, *Bacillus cereus, Bacillus anthracis* and *Bacillus thuringiensis*), *Bacteroides* spp. (including, for example, *B. fragilis, B. thetaiotaomicron, B. vulgatus, B. ovatus, B. distasonis, B. uniformis, B. stercoris, B. eggerthii, B. merdae,* and *B. caccae*), *Campylobacter* spp. (including, for example, *Campylobacter jejuni, Campylobacter laridis,* and *Campylobacter hyointestinalis*), *Clostridium* spp. (such as the pathogenic clostridia including all types of *Clostridium botulinum* (including those in Groups I, II, III and IV, and including those that produce botulism A, B, C, D, E, F and G), all types of *Clostridium tetani*, all types of *Clostridium difficile*, and all types of *Clostridium perfringens*), *Ebola* spp. (e.g. EBOV Zaire), *Enterobacter* spp. (including, for example, *Enterobacter aerogenes* (also sometimes referred to as *Klebsiella mobilis*), *Enterobacter agglomerans* (also sometimes referred to as *Pantoea agglomerans*), *Enterobacter amnigenus, Enterobacter asburiae, Enterobacter cancerogenus* (also sometimes referred to as *Enterobacter taylorae* and/or *Erwinia cancerogena*), *Enterobacter cloacae, Enterobacter cowanii, Enterobacter dissolvens* (also sometimes referred to as *Erwinia dissolvens*), *Enterobacter gergoviae, Enterobacter hormaechei, Enterobacter intermedium, Enterobacter intermedius* (also sometimes referred to as *Enterobacter intermedium*), *Enterobacter kobei, Enterobacter nimipressuralis* (also sometimes referred to as *Erwinia nimipressuralis*), *Enterobacter sakazakii*, and *Enterobacter taylorae* (also sometimes referred to as *Enterobacter cancerogenus*)), *Enterococcus* spp. (including, for example, Vancomycin Resistant Enterococcus (VRE), *Enterococcus faecalis, Enterococcus faecium, Enterococcus durans, Enterococcus gallinarum*, and *Enterococcus casseliflavus*), *Escherichia* spp. (including the enterotoxigenic (ETEC) strains, the enteropathogenic (EPEC) strains, the enterohemorrhagic (EHEC) strain designated *E. coli* O157:H7, and the enteroinvasive (EIEC) strains), *Gastrospirillum* spp. (including, for example, *Gastrospirillum hominis* (also sometimes now referred to as *Helicobacter heilmannii*), *Helicobacter* spp. (including, for example, *Helicobacter pylori* and *Helicobacter hepaticus*), *Klebsiella* spp. (including, for example, *Klebsiella pneumoniae, Klebsiella ozaenae, Klebsiella rhinoscleromatis, Klebsiella oxytoca, Klebsiella planticola, Klebsiella terrigena*, and *Klebsiella ornithinolytica*), *Salmonella* spp. (including, for example, *S. typhi* and *S. paratyphi* A, B, and C, *S. enteritidis*, and *S. dublin*), *Shigella* spp. (including, for example, *Shigella sonnei, Shigella boydii, Shigella flexneri*, and *Shigella dysenteriae*), *Staphylococcus* spp. (including, for example, *Staphylococcus aureus*, methicillin-resistant *Staphylococcus aureus* (MRSA), *Staphylococcus saprophyticus* and *Staphylococcus epidermis*), *Streptococcus* ssp. (including Groups A (one species with 40 antigenic types, *Streptococcus pyogenes*), B, C, D (five species (*Streptococcus faecalis, Streptococcus faecium, Streptococcus durans, Streptococcus avium*, and *Streptococcus bovis*)), F, and G, including *Streptococcus pneumoniae*), *Pseudomonas* spp. (including, for example, *Pseudomonas aeriginosa, Pseudomonas maltophilia, Pseudomonas fluorescens, Pseudomonas putida, Pseudomonas cepacia, Pseudomonas stutzeri, Pseudomonas mallei, Pseudomonas pseudomallei* and *Pseudomonas putrefaciens*), *Vibrio* spp. (including, for example, *Vibrio cholera* Serogroup O1 and *Vibrio cholera* Serogroup Non-O1, *Vibrio parahaemolyticus, Vibrio alginolyticus, Vibrio furnissii, Vibrio carchariae, Vibrio hollisae, Vibrio cincinnatiensis, Vibrio metschnikovii, Vibrio damsela, Vibrio mimicus, Vibrio vulnificus*, and *Vibrio fluvialis*), *Yersinia* spp. (including, for example, *Yersinia pestis, Yersinia enterocolitica* and *Yersinia pseudotuberculosis*), *Neisseria, Proteus, Citrobacter, Aerobacter, Providencia, Serratia, Brucella, Francisella tularensis* (also sometimes referred to as *Pasteurella tularensis, Bacillus tularensis, Brucella tularensis*, tularemia, rabbit fever, deerfly fever, Ohara's disease, and/or Francis disease), and the like. Thus, for example, various bacterial infections or unwanted levels of bacteria that can be treated, prevented or addressed by the present inactivated agents include but are not limited to those associated with anthrax (*Bacillus anthracis*), staph infections (*Staphylococcus aureus*), typhus (*Salmonella typhi*), food poisoning (*Escherichia coli*, such as O157:H7), bacillary dysentery (*Shigella dysenteria*), pneumonia (*Psuedomonas aerugenosa* and/or *Pseudomonas cepacia*), cholera (*Vibrio cholerae*), ulcers (*Helicobacter pylori*), *Bacillus cereus, Salmonella, Clostridium perfringens, Campylobacter, Listeria monocytogenes, Vibrio parahaemolyticus*, botulism (*Clostridium botulinum*), smallpox (variola major), listeriosis (*Listeria monocytogenes*), tularemia (*Francisella tularensis*), plague (*Yersinia pestis*; also sometimes referred to as bubonic plague, pneumonic plague, and/or black death) and others. *E. coli* serotype 0157:H7 has been implicated in the pathogenesis of diarrhea, hemorrhagic colitis, hemolytic uremic syndrome (HUS) and thrombotic thrombocytopenic purpura (TTP). As indicated herein, the inactivated agents of the invention are also active against drug-resistant and multiply-drug resistant strains of bacteria, for example, multiply-resistant strains of *Staphylococcus aureus* and vancomycin-resistant strains of *Enterococcus faecium* and *Enterococcus faecalis*.

Fungal infections that can be treated or prevented by the present inactivated agents include infections by fungi that infect a mammal, including *Histoplasma capsulatum, Coccidioides immitis, Cryptococcus neoformans, Candida* ssp. including *Candida albicans, Aspergilli* ssp. including *Aspergillus fumigatus, Sporothrix, Trichophyton* ssp., *Fusarium* ssp., *Tricosporon* ssp., *Pneumocystis carinii*, and *Trichophyton mentagrophytes*. Hence, for example, infections or unwanted levels of target fungi can be treated, prevented or addressed by the present inactivated agents. Such fungi also include fungal pathogens that may have potential for use biological weapons, including *Coccidioides immitis* and *Histoplasma capsulatum.*

Anti-microbial activity can be evaluated against these varieties of microbes (viruses, bacteria, fungi and parasites) using methods available to one of skill in the art. In one embodiment, anti-microbial activity is the amount of the inactivated agent that stimulates an immune response against the microbe. In another embodiment, anti-microbial activity is the amount of the inactivated agent that effectively immunizes a mammal against the microbe.

Treatment of, or treating, cancer is intended to include the alleviation of or diminishment of at least one symptom typically associated with the disease. The treatment also includes alleviation or diminishment of more than one symptom. The treatment may cure the cancer, e.g., it may reduce the number of cancer cells and/or arrest the growth of the cancerous tumor.

Cancers that can be treated by the present inactivated agents include solid mammalian tumors as well as hematological malignancies. Solid mammalian tumors include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin central nervous system; sarcomas of the soft tissue and bone; and melanoma of cutaneous and intraocular origin. Hematological malignancies include childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Information regarding numerous types of cancer can be found, e.g., from the American Cancer Society (www.cancer.org), or from, e.g., Wilson et al. (1991) Harrison's Principles of Internal Medicine, 12.sup.th Edition, McGraw-Hill, Inc. Both human and veterinary uses are contemplated.

Anti-cancer activity can be evaluated against varieties of cancers using methods available to one of skill in the art. Anti-cancer activity, for example, is determined by identifying the $LD_{100}$ or $ED_{50}$ of an inactivated tumor or cancer cell of the present invention that prevents the growth of a cancer. In one embodiment, anti-cancer activity is the amount of the inactivated agent that effectively immunizes a mammal against that cancer type.

According to the present invention, the inactivated agents provided herein do not have substantial or undesired toxicity or infectivity within the mammalian organism to be treated.

Administration of the Inactivated Agents

The inactivated agents (e.g., inactivated viruses) of the invention are administered so as to achieve a reduction in at least one symptom associated with an infection, cancer, tumor or other disease, or a decrease in the amount of antibody associated with the infection, cancer, tumor or other disease.

To achieve the desired effect(s), the inactivated agent, or a combination of inactivated agents, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results.

In some embodiments, the dosage is measured by the number of viral particles or the number of cells. Thus, for example, about 20 to about 50,000 inactivated viral particles or inactivated cells can be administered, or about 50 to about 25,000 inactivated viral particles or inactivated cells can be administered, or about 100 to about 10,000 inactivated viral particles or inactivated cells can be administered.

The amount administered will vary depending on various factors including, but not limited to, the inactivated agent chosen, the disease, the weight, the physical condition, the health, the age of the mammal, or whether prevention or treatment is to be achieved. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the inactivated agents of the invention is generally intermittent over a preselected period of time, for example, in a series of spaced doses. Both local and systemic administration is contemplated.

To prepare the composition, inactivated agents are prepared according to the methods described herein, and purified as necessary or desired. In some embodiments the inactivated agents can be lyophilized and/or stabilized. The inactivated agent can then be adjusted to the appropriate concentration, and optionally combined with other agents.

The absolute weight of a given inactivated agent included in a unit dose can vary widely. For example, about 0.01 to about 2 g, or about 0.1 to about 500 mg, of at least one inactivated agent of the invention, or a plurality of inactivated agents, can be administered. Alternatively, the unit dosage can vary from about 0.01 g to about 5 g, from about 0.01 g to about 3.5 g, from about 0.01 g to about 2.5 g, from about 0.1 g to about 1 g, from about 0.1 g to about 0.8 g, from about 0.1 g to about 0.4 g, or from about 0.1 g to about 0.2 g.

One or more suitable unit dosage forms comprising the therapeutic inactivated agents of the invention can be administered by a variety of routes including oral, parenteral (including subcutaneous, intravenous, intramuscular and intraperitoneal), rectal, dermal, transdermal, intrathoracic, intrapulmonary, mucosal and intranasal (respiratory) routes. In some embodiments, the agents of the invention are administered by mucosal, intranasal, or subcutaneous routes.

In some embodiments, the agents of the invention are administered by injection. The therapeutic inactivated agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic inactivated agents of the invention are prepared for oral administration, they are generally combined with a pharmaceutically acceptable carrier, diluent or excipient to form a pharmaceutical formulation, or unit dosage form. For oral administration, the inactivated agents may be present as a powder, a granular formulation, a solution, a suspension, an emulsion or in a natural or synthetic polymer or resin for ingestion of the agents from a chewing gum. The inactivated agents may also be presented as a bolus, electuary or paste. Orally administered therapeutic inactivated agents of the invention can also be formulated for sustained release, e.g., the inactivated agents can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic inactivated agents of the invention can be prepared by procedures known in the art using well-known and readily available ingredients. For example, the inactivated agent can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the inactivated agents of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one inactivated agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more inactivated agents of the invention are designed to resist disintegration in the stomach and dissolve in the more neutral to alkaline environment of the duodenum.

The inactivated agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic inactivated agents of the invention can also take the form of an aqueous or anhydrous solution or dispersion, or alternatively the form of an emulsion or suspension or salve.

Thus, the therapeutic inactivated agents may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The inactivated agents and other ingredients may form suspensions, solutions, or emulsions in oily or aqueous vehicles, and may contain formulatory agents such as suspending, stabilizing and/or dispersing agents. Alternatively, the inactivated agents and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if desired, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Also contemplated are combination products that include one or more inactivated agents of the present invention and one or more other anti-microbial agents. For example, a variety of antibiotics can be included in the pharmaceutical compositions of the invention, such as aminoglycosides (e.g., streptomycin, gentamicin, sisomicin, tobramycin and amicacin), ansamycins (e.g. rifamycin), antimycotics (e.g. polyenes and benzofuran derivatives), β-lactams (e.g. penicillins and cephalosporins), chloramphenical (including thiamphenol and azidamphenicol), linosamides (lincomycin, clindamycin), macrolides (erythromycin, oleandomycin, spiramycin), polymyxins, bacitracins, tyrothycin, capreomycin, vancomycin, tetracyclines (including oxytetracycline, minocycline, doxycycline), phosphomycin and fusidic acid.

Additionally, the inactivated agents are well suited to formulation as sustained release dosage forms and the like. The formulations can be so constituted that they release the inactivated agent, for example, in a particular part of the intestinal or respiratory tract, possibly over a period of time. Coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the inactivated agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic inactivated agents of the invention can be delivered via patches or bandages for dermal administration. Alternatively, the inactivated agent can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The inactivated agents can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the inactivated agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic inactivated agent may further be formulated for topical administration in the nose, mouth or throat. For example, the active ingredients may be formulated as a lozenge further comprising a flavored base, for example, sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The inactivated agents of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, cancer, tumor or disease. Any statistically significant attenuation of one or more symptoms of an infection, cancer, tumor or disease that has been treated pursuant to the methods of the present invention is considered to be a treatment or prevention of such infection, cancer, tumor or disease within the scope of the invention.

Alternatively, for administration by inhalation or insufflation, the composition may take the form of a solution or a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in AEROSOLS AND THE LUNG, Clarke, S. W. and Davia, D. eds., pp. 197-224, Butterworths, London, England, 1984).

Therapeutic inactivated agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the inactivated agents of the present invention specific for the indication or disease to be treated or prevented. Dry aerosol in the form of finely divided solid inactivated agent that are not dissolved or suspended in a liquid are also useful in the practice of the present invention.

Inactivated agents of the present invention may be formulated as dusting powders and comprise finely divided particles having an average particle size of between about 1 and 5 µm, alternatively between 2 and 3 µm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating or preventing the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic inactivated agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, antihistamines, bronchodilators and the like, whether for the conditions described or some other condition.

The present invention further pertains to a packaged pharmaceutical composition for controlling microbial infections or cancer such as a kit or other container. The kit or container holds a therapeutically effective amount of a pharmaceutical composition for controlling microbial infections, or cancer or tumor growth and instructions for using the pharmaceutical composition for control of the microbial infection or for control of the cancer or tumor. The pharmaceutical composition includes at least one inactivated agent of the present invention, in a therapeutically effective amount such that microbial infection, cancer or tumor is controlled.

The invention is further illustrated by the following non-limiting Examples.

EXAMPLE 1

Illustrative Materials and Methods

This Example provides many of the reagents and procedures employed for several experiments with SIV and/or HIV.
Materials and Methods Antibodies and their sources were as follows: anti-HLA-DR IgG L243 (mAb from Elena Chertova), anti-HLA-DR IgG DA6-147 (mAb from Paul Roche), and anti-Gp32 IgG (rabbit polyclonal Ab from Raoul Benveniste). [$^{125}$I]INA (300 mCi/mmol) was purchased from Lofstrand Laboratories (Gaithersburg, Md.). All other biochemical reagents used were of the highest purity available and were obtained from regular commercial sources.

Viruses. HIV-1$_{MN}$/H9 clone 4 was propagated in H9 cells, as described previously (Ott at al. 1995). SIVmne was obtained from supernatants of the cloned E11 S cell lines derived from a culture of HuT-78 cells infected with SIVmne (Benveniste at al. 1990). Concentrated virus preparations were produced by sucrose gradient banding in a continuous-flow centrifuge (Bess at al. 1997). Inactivation of SIV by treatment with aldrithiol-2 was performed as described (Rossio at al. 1998).

Cell cultures. Ghost-345 cells (derived from human osteosarcoma cells) that stably express CD4, as well as CXCR4 and CCR5, and NIH3T3 CD4/X4 were obtained from Dan Littman and Vineet KewalRamani. TF228 cells derived from the BJAB human B cell line and that stably express the HIV-1$_{LAI}$ envelope glycoprotein (Jonak at al. 1993) were from Zdenka L. Jonak (Smith-Kline & Beecham, King of Prussia, Pa.). SupT1 (human CD4-expressing T-Lymphoblastic cell line) and TF228 were grown in RPMI supplemented with 10% fetal bovine serum (FBS) (Life Technologies, Inc., Rockville). NIH3T3 CD4 cells were grown in Dulbecco's modified Eagle's medium+10% FBS (D10). NIH3T3 CD4/X4 cells were grown in D10+3 mg/ml puromycin. Ghost 345 cells were grown in D10+500 mg/ml G418+100 mg/ml hygromycin+1 mg/ml puromycin. All the cells were grown in the presence of penicillin and streptomycin.

Treatment with INA. Viruses or cells were suspended in Phosphate Buffered saline (PBS) at a concentration of 0.5-1.0 mg/ml. A stock solution of 30 mM INA in DMSO was prepared. INA was added to the cell or viral suspension under dim light to a final concentration of 1-200 µM. The INA was added so that the total DMSO will not exceed 1% of the total sample volume. Addition of INA was done in installments of 3-4 aliquots while mixing vigorously after each aliquot. The sample was incubated at room temperature for 30 minutes and washed once in PBS.

The suspension was then irradiated with an ozone free 100 W mercury arc lamp and through a water filter to eliminate heat and a 320 nm cut-off filter. Time of irradiation vary with the size of the sample. For a 1 ml sample and a cross-area of 1 cm$^2$ the irradiation time was 2 minutes. For a 20 ml sample and a cross area of 10 cm$^2$ the irradiation time was 5 minutes.

Labeling of the target cells. The fluorescent lipid DiO (Molecular Probes, Eugene, Oreg.) was diluted in 50% Diluent C (Sigma-Aldrich, St. Louis, Mo.) and 50% serum-free RPMI (RPMI) to a final concentration of 50 mM. After two washes in RPMI the cells were incubated in the DiO solution for 30 min at room temperature. They were then washed once with clear RPMI and further incubated 30 min in medium at room temperature. They were then washed three times with PBS, in which they were finally resuspended. At this point [$^{125}$I]INA (1 Ci/mmol) was added in the amount of 10 mCi for each experimental group. Upon 20 min incubation in the dark, the cells were washed with PBS and subsequently used for the photolabeling experiment.

Virus infectivity assay. The infectivity of HIV-1(MN) and SIV Mne samples was determined by using AA2 clone 1 and clone 5 cells, respectively, as described by Raviv et al., Virology 293:243-251 (2002). Cells were cultured in RPMI 1640 supplemented with 10% heat-inactivated fetal bovine serum, 2 mM L-glutamine, 100 U/ml penicillin, 100 µg/ml streptomycin, 0.1 µg/ml gentamicin, and 20 mM HEPES buffer. To determine infectious titers of untreated virus, serial dilutions of the virus were prepared in cell culture medium. One hundred microliters of virus from each dilution was added to 2.5×10$^6$ cells in 0.9 ml of medium (resulting in an additional 1:10 dilution of the virus) and incubated at 37° C. in a 15-ml tube for 18 h while being slowly rocked. After the addition of 9 ml of incomplete medium, the cells were washed to remove unbound virus. The cells were washed twice more, and the pellet was resuspended in 5 ml of complete medium. One milliliter (5×10$^5$ cells) was placed in each of 4 wells of a 24-well plate (Costar no. 3524). Mock-infected cells were included as negative controls for each set of titrations. Plates were incubated at 37° C. in a humidified, 5% CO$_2$ incubator. On day 3, 1 ml of complete medium was added to each well. These cultures were passaged by removing 50% of the culture and adding fresh medium on days 3, 7, 10, 14, 17, and 21 to maintain actively dividing cell populations. On days 7, 14, and 21, samples were analyzed for viral capsid protein concentration to determine if progeny virions could be detected.

These samples were clarified from cells by centrifugation at 600×g for 5 min, and the supernatant was lysed by the addition of a $\frac{1}{10}$ volume of 10% Triton X-100. Capsid protein concentrations were determined using either an SIV p28 or HIV-1 p24 antigen capture assay (house assay kits; AIDS Vaccine Program, SAIC). Samples were considered positive if they produced capsid protein concentrations above the antigen capture assay cutoff value and these concentrations increased over time. Infectious titers were determined by the Reed and Muench method (Roos et al., Virology 273:307-315 (2000)) using capsid concentration results from day 21.

Infectivity assay of INA-treated virus. To determine if INA-treated virus preparations were free of detectable infectious virus, samples were analyzed at the lowest possible dilution and against a greater number of target cells: 0.5 ml of INA-treated virus was added to 1.25×10$^7$ cells in 2.5 ml of medium and incubated at 37° C. in a 15-ml tube for 18 h while being slowly rocked. Due to the high concentration of virus in the inoculum, these samples were washed four times by centrifugation to remove unbound virus. The resulting cell pellets were resuspended in 25 ml of medium (final cell concentration was 5.0×10$^5$/ml), planted in T75 flasks, and incubated at 37° C. in 5% CO$_2$. These cultures were passaged and analyzed for capsid antigen concentration. All the other details were as described above for the untreated virus.

Measurement of fusion by photo-sensitized labeling. The HLA-DR$^+$ virions are incubated with the HLA-DR$^-$ target cells labeled with the fluorescent lipid analog 3,3'-dioctadecyloxacarbocyanine (DiO) and [$^{125}$I]INA for binding at room temperature. Plasma membranes of target cells bearing CD4 and coreceptors are labeled with the fluorescent lipid analog 3-dioctadecyloxa-carbocyanine (DiO). [$^{125}$I]INA spontaneously partitions from the medium into viral and other target membranes. In the bound state only integral membrane proteins of the DiO-labeled target membranes react with [$^{125}$I]INA following photoactivation by visible light. Upon incubation of virus-cell complexes at 37° C., DiO becomes part of the viral membrane as a result of fusion and therefore photoactivation using visible light results in covalent attachment of [$^{125}$I]INA to viral membrane-resident proteins. At different times following incubation at 37° C., samples are irradiated with visible light, the cells are lysed, and the HIV or SIV Env, as well other viral envelope-resident proteins such as HLA-DR, is isolated from other radioactively labeled proteins by immunoprecipitation. The extent of radioactivity incorporated into these proteins is then a quantitative measure of viral fusion at the plasma membrane level.

In the case of HIV-1, 1 ml virus (0.79 mg/ml capsid) was added to 3×10$^8$ SupT1 cells in 3 ml. In case of SIVmne, 0.2 ml of virus (0.084 mg/ml capsid) was added to 3 ml medium overlaid on attached Ghost-345 cells. The unbound virions were then removed and the samples subjected to fusion at the desired temperature. At defined times cells were irradiated with an argon laser (Lexel Laser, Inc., Freemont, Calif.) in the multiline mode of 488/514 nm. Suspension cells were irradiated horizontally for two consecutive 10-s periods with a beam of 400 mW that was passed through a UV cut-off filter and focused on an area of 1 cm$^{-2}$ (133 mW/cm$^2$/min). Plated cells were irradiated for 60 s vertically using a 5-W beam focused on an area of 144 cm$^2$ (11 mW/cm$^2$/min).

The cells were then collected and lysed (2% Triton X-100 in Tris-buffered saline (TBS; 50 mM Tris, 138 mM NaCl, 2. mM KCl, pH 8) containing protease inhibitors) for 2 h at 4° C. The insoluble material was spun down at 15,000 rpm for 15 min in an Eppendorf microcentrifuge. The supernatant was then diluted twice in TBS and total protein was measured using the BCA protein determination reagent (Pierce, Rockford, Ill.). Samples were subjected to immunoprecipitation using L243 (for HLA-DR) or anti-SIV gp32 for the SIV Env. Upon overnight incubation with the respective antibody, protein G-agarose was added for 2 h and washed five times with TBS containing 1% Triton X-100. Proteins were separated by 14% SDS-PAGE and transferred to nitrocellulose membranes. Blots were incubated for 1 h in PBST (phosphate-buffered saline, 0.2% Tween 20) containing 5% powdered skim milk. Membranes were incubated for 2 h with the primary antibody in a 3% BSA solution containing 0.2% Tween 20 and for 1 h 30 min with a peroxidase-conjugated secondary antibody in PBST. Immunoreactivity was detected by using an ECL kit (Amersham, Piscataway, N.J.) and an imaging system with high dynamic range (Bio-Rad GS 505 Molecular Imager System, Hercules, Calif.). The blots were then exposed to Phosphorimager screens; bands were quantified using a Storm system (Molecular Dynamics Sunnyvale, Calif.) and the Image Quant software (Molecular Dynamics).

HIV-1 envelope glycoprotein-mediated cell-cell fusion. For the photo-sensitized labeling experiments HLA-DR+ TF228.1.16 effector cells and DiO-labeled HLA-DR target cells were loaded with [$^{125}$I]INA and incubated for various times at 37° C. The plates were irradiated for 60 s with a 5-W laser beam over an area of 144 cm$^2$ (11 mW/cm$^2$/min) and incorporation of [$^{125}$I]INA into HLA-DR was measured as described above. For the dye redistribution experiments target cells were labeled with the cytoplasmic dye 5- and 6-([(4-chloromethyl)benzoyl]amino)tetramethylrhodamine (CMTMR) at a concentration of 1.5 mM for 1 h at 37° C. Envelope-expressing cells were labeled with calcein AM at a concentration of 1 mM for 1 h at 37° C. Calcein-labeled effector cells were co-cultured with CMTMR-labeled target cells for 2 h at 37° C., and dye redistribution was monitored microscopically as described previously (Munoz-Barroso et al. 1998). The extent of fusion was calculated as:

$$\text{percent fusion} = \frac{100 \times \text{number of bound cells positive for both dyes}}{\text{number of bound cells positive for } CMTMR}$$

EXAMPLE 2

INA-Treated SIV Cannot Fuse with Mammalian Cells

This Example describes the results of experiments showing that INA treatment inactivates viruses but leaves them substantially intact. However, such treatment inhibits viral fusion with host cells and prevents viral infection.

FIG. 1 shows a Coomassie-stained SDS-PAGE gel illustrating that treatment of SIV virions with INA causes insubstantial changes in the molecular weights of viral proteins. As shown, exposure to INA at concentrations ranging from 2 µM to 200 µM caused substantially no change in the separation pattern of SIV proteins as compared to untreated virions (DMSO) and virions that were treated with either TNE (0.1 M Tris HCl, 0.1 M NaCl, 1 mM EDTA) or 200 µM INA but not exposed to light. Similar results were obtained when these experiments were repeated with HIV. These results indicate that INA treatment maintains the integrity of the majority of viral proteins.

However, as shown by reverse phase HPLC analysis of viral proteins under reducing conditions (FIG. 2), many viral proteins were modified to some extent by INA. As a result, the migration patterns of these viral proteins on the HPLC column were altered. But even though there are some changes in viral proteins after treatment with INA, several major viral proteins were still recognized by monoclonal antibodies directed against those proteins (FIG. 3). Hence, for example, the GP120, P28 and GP32 proteins from INA-treated virions were recognized by monoclonal antibodies directed against the respective untreated proteins.

When INA was used to treat SIV, viral infectivity was reduced to zero (FIG. 4). Incubation of the SIV-infected cells for up to 11 days after INA treatment showed that a dose-dependent decrease in the production of the viral protein, p28, occurred with no detectable production when 200 µM INA was used (FIG. 4). Similar results were obtained when infectivity was measured on INA-treated HIV after 21 days (Table 1).

Thus, the infectivity of SIV was 100% blocked by treatment with appropriate levels of INA. Table 1 illustrates that INA treatment completely blocks infection of SIV and HIV as measured by the expression of the viral protein P-28 for SIV and P-24 for HIV at different times after the introduction of the virus. In particular, at 200 µM INA infectivity was blocked by 100%.

TABLE 1

Infectivity of control and INA-treated HIV and SIV established by capsid production after 21 days of culture.

SP1061 - INA Treatment of Infectious SIV Mne/HuT78 clone E11S lot P3932
Infectivity assay vs. AA2 clone 5 cells

| SIV Mne | | Avg. Capsid Protein conc. (pg/ml)[1] | | | Culture Result[2] | | |
|---------|------|--------|--------|--------|-----|-----|------------------|
| CL. E11S | 1/dil | Day 7 | Day 14 | Day 21 | Pos | Neg | 1/TCID$_{50}$/ml[3] |
| Control | 10$^3$ | 21,669 | 76,680 | 67,525 | 4 | 0 | 2.2 × 10$^6$ |
|         | 10$^4$ | 1,263  | 71,517 | 60,856 | 4 | 0 | |
|         | 10$^5$ | 0      | 62,876 | 70,193 | 4 | 0 | |
|         | 10$^6$ | 0      | 18,334 | 48,966 | 3 | 1 | |
|         | 10$^7$ | 0      | 0      | 0      | 0 | 4 | |
|         | 10$^8$ | 0      | 0      | 0      | 0 | 4 | |

TABLE 1-continued

| Infectivity of control and INA-treated HIV and SIV established by capsid production after 21 days of culture. | | | | | | | |
|---|---|---|---|---|---|---|---|
| INA | $10^1$ | 0 | 0 | 0 | 0 | 0 | 0 |
| SP1122 - INA Treatment of Infectious HIV-1(MN)/H9 CL. 4 lot P3941 Infectivity assay vs. AA2 clone 1 cells | | | | | | | |
| HIV-1 | | Avg. Capsid Protein conc. (pg/ml)[1] | | | Culture Result[2] | | |
| (MN) | 1/dil | Day 7 | Day 14 | Day 21 | Pos | Neg | $1/TCID_{50}/ml$[3] |
| Control | $10^3$ | 213,795 | 188,411 | 588,818 | 4 | 0 | $4.6 \times 10^4$ |
| | $10^4$ | 6,317 | 41,027 | 503,443 | 4 | 0 | |
| | $10^5$ | 375 | 0 | 0 | 1 | 3 | |
| | $10^6$ | 0 | 0 | 0 | 0 | 4 | |
| | $10^7$ | 0 | 0 | 0 | 0 | 4 | |
| | $10^8$ | 0 | 0 | 0 | 0 | 4 | |
| INA | $10^1$ | 9,201 | 0 | 0 | 0 | 4 | 0 |
| | $10^2$ | 0 | 0 | 0 | 0 | 4 | |
| | $10^3$ | 0 | 0 | 0 | 0 | 4 | |
| | $10^4$ | 0 | 0 | 0 | 0 | 4 | |
| | $10^5$ | 0 | 0 | 0 | 0 | 4 | |
| | $10^6$ | 0 | 0 | 0 | 0 | 4 | |

[1]Average of determined capsid protein concentrations from quadruplicate cultures.
[2]Culture result as assessed on day 21. "Pos" indicates the number of the quadruplicate cultures that became productively infected with virus. "Neg" indicates the number of cultures that remained uninfected.
[3]Reciprocal Tissue Culture Infectious Dose 50 was determined from the culture result data using the Method of Reed and Muench (Roos et al., Virology 273: 307-315 (2000)).
[4]Negative control cultures were maintained and remained uninfected though out the 21 day test period.

Even though INA-treated virions can bind to host cells, they exhibit substantially reduced fusion with those host cells. As shown by FIG. 5, INA treatment blocked fusion of SIV with the target cell at the plasma membrane level, as measured by a photosensitized labeling method developed by the inventors (see Example 1). Hence, the types of minor structural changes caused by INA treatment appear to be sufficient to undermine the functioning of the viruses.

These data indicate that INA treatment gives rise to viral particles that have minor but significant structural changes. The structural changes do not affect the ability of the viral particles to be recognized by antibodies (FIGS. 3 and 7). However, INA treatment inhibits viral fusion with host cells (FIG. 5). Even more importantly, INA treatment substantially eliminates viral infectivity (FIG. 4 and Table 1). Hence, INA is a useful reagent for inactivating infectious agents, for example, so that those inactivated infectious agents may be used as vaccines.

EXAMPLE 3

INA-Treated HIV

Are Transcriptionally Inactive in Mammalian Cells

This Example describes the results of experiments showing that INA treatment inactivates human immunodeficiency viral transcription, thereby illustrating by another procedure that INA treatment inactivates HIV.

Infectivity assay was carried out using the luciferase reporter gene assay, essentially as described in Spenlehauer, C., Gordon, C., Trkola, A. and Moore, J. (2001) Virology 280, 292-300; and Wei, X., Decker, J., Liu, Z., Zhang, Z., Arani, R., Kilby, M., Saag, M., Wu, X., Shaw, G., and Kappes, J. (2002) Antimicrobial Agents and Chemotherapy, 46, 1896-1905.

Briefly, JC53BL cells were used that express the luciferase enzyme under the transcriptional control of HIV long terminal repeat (LTR). Upon HIV infection the TAT protein from the virus binds to the LTR to induce the expression of Luciferase. The level of Luciferase expression can be assessed by incubation of the sample with a luciferase substrate which triggers a chemiluminescent signal that can be easily quantified by a luminometer.

As shown in FIG. 6, substantially no luciferase expression is detected after JC53BL cells were exposed to INA-treated HIV. However, HIV viruses that were not exposed to INA readily induced expression of luciferase.

These results further demonstrate the effectiveness of INA for inactivating HIV. No effective vaccines are currently available for preventing HIV infection. However, the results provided herein indicate that the present compositions involving INA-inactivated HIV may be useful as vaccines.

EXAMPLE 4

INA-Treated HIV Bind to Neutralizing Anti-HIV Antibodies

This Example describes the results of experiments showing that INA treatment does not destroy the antigenicity of HIV. Instead, INA-treated HIV readily binds to available anti-HIV neutralizing antibodies.

The antibodies employed were the 2G12 and B12 antibodies that target Gp120 and the 4E10 antibody that targets gp41. Each of these antibody preparations is broadly neutralizing of HIV infectivity.

Antibody binding to HIV virions was measured by an immunocapture procedure essentially as described in Nyambi, P., Burda, S., Bastani, L., and Williams, C. (2001) Journal of Immunological Methods, 253, 253-262. Briefly, 10 microgram of each antibody was coated onto 96 well ELISA plates and non-specific binding was blocked with BSA. HIV was then added and incubated for binding for one hour at 37° C. using different amounts of virus as indicated in FIG. 7. A control assay was performed in which no antibody was used.

After washing, the samples were lysed and analyzed for the presence of virus by measuring the viral protein, p24, using an ELISA assay. Each experimental point was carried out in triplicate.

The results are provided in FIG. 7. As shown, FIG. 7 illustrates that INA-treated HIV interacts substantially the same as the non-treated virus with all three antibody preparations. These antibodies were originally derived from human AIDS patients that developed these antibodies spontaneously. Cells producing these antibody preparations were cloned to generate anti-HIV monoclonal antibody preparations. Each of these human monoclonal antibody preparations specifically recognizes structural epitopes on HIV envelope proteins. The 2G12 and B12 antibodies recognize epitopes on the gp120 protein and the 4E10 antibodies recognize an epitope on the gp41 fusion protein. These three antibody clones are broadly neutralizing, i.e. they block infection by many types of HIV in cell culture assays. Hence, these antibodies probe epitopes on HIV that have the potential of inducing antibodies in humans that will block viral infections.

As illustrated herein, each of these antibody preparations recognizes and binds to INA-inactivated HIV, demonstrating that the epitopes recognized by the antibodies are substantially unaffected by INA treatment.

EXAMPLE 5

Administration of INA-Treated Ebola Viruses

Protect Mice Against Ebola Infection

This Example illustrates that a single immunization of mice with INA-inactivated Ebola virus in the absence of adjuvant resulted in protection against a lethal challenge with 1000 pfu of mouse adapted Ebola virus. INA treatment resulted in complete loss of Ebola viral infectivity of cultured mammalian cells. Electron microscopy combined with immunogold staining as well as virus capture assays indicated that conformational epitopes were preserved on the surface of the virus. Mice injected with 50,000 pfu of INA-inactivated mouse-adapted Zaire-EBOV survived with no sign of disease. Interestingly, INA-inactivated virus, but not irradiated virus, was capable of inducing a short term protective response in 100% of mice when administered 3 days before challenge. These data indicate that INA has significant potential for development of filovirus vaccine and therapeutic agents useful against viral infection.

Materials and Methods

Reagents and cells. Vero E6 cells were cultured in DMEM supplemented with glutamine and 10% fetal calf serum at 37° C. in a humidified $CO_2$ incubator. Anti-Ebola GP monoclonal antibodies were kindly provided by Dr. Mary-Kate Hart (US-AMRIID).

Filoviruses. The EBOV Zaire strain of Ebola virus was used for many of these studies. A recombinant Zaire Ebola virus expressing the gene for green fluorescent protein (GFP-EBOVZ) was kindly provided by Dr. Jason Paragas (USAMRIID). EBOV-Zaire virus was propagated and enumerated by standard plaque assay on Vero or Vero E6 cells (Moe et al. J Clin Microbiol 13:791-3 (1981)). The virus was band purified over a sucrose gradient as described by Warfield et al., Proc. Natl. Acad. Sci. USA 100:15889-94 (2003); and Hevey et al. Virology 239: 206-16 (1997). EBOV-infected cells and animals were handled by qualified personnel under maximum containment in a biosafety level (BSL)-4 laboratory at the United States Army Medical Research Institute of Infectious Diseases.

Treatment of virus with INA. Mouse-adapted EBOV-Zaire or GFP-EBOVZ were diluted in phosphate-buffered saline (PBS) to a final concentration of $2 \times 10^6$ pfu/ml. INA from a stock of 30 mM in dimethyl sulfoxide (DMSO) was added to the virus suspension under dim light in three to four installments (for uniform mixing) to final concentrations as indicated in the individual experiments. The suspension was incubated for 30 min at room temperature. Glutathione, reduced form, was added to the suspension to final concentrations between 20 to 30 mM to neutralize any residual INA in the aqueous phase, and the sample was irradiated with UV light. The light source was a 100-W ozone-free mercury arc lamp placed in a lamphouse with a collector lens (Olympus). Samples were irradiated through a 310-nm cutoff filter placed in front of the lens (to allow transmission of the 313-, 334-, and 365-nm mercury emission bands) and through a water filter (to prevent sample heating) at a distance of 5 cm from the light source. At that point, the light dose was 10 mW/cm$^2$ s. Irradiation times were 5 min for sample volumes of up to 1 ml in a clear microcentrifuge tube.

Detection of Virus infectivity using GFP-EBOVZ: Vero cells were infected with GFP-EBOVZ at an multiplicity of infection (MOI) of 5. Infected cells were detected after various time point post infection by flow cytometry.

Real time polymerase chain reaction for detection of EBOV genome: RNA was extracted from test samples by the TRIzol LS reagent (Invitrogen, Carlsbad, Calif.) according to the manufacturer's directions. RNA pellets were dissolved in 100 uL of RNase free water and stored at −80° C. until used. The primers were synthesized using phosphoramidite chemistry on an ABI 394 DNA/RNA synthesizer (ABI Biosystems, Foster City, Calif.). The TaqMan® probes were synthesized with the fluorescent dyes FAM at the 5' terminus and TAMRA at the 3' terminus (ABI Biosystems). Real time One-Step RT-PCR assay combining Superscript reverse transcriptase with Platinum Taq polymerase (Invitrogen) and TaqMan probe assay were used. The reactions were carried out in at total volume of 20 uL. Each reaction contained 0.2 mM dNTP, 0.4 uL of RT/Platinum Taq mix (Invitrogen), 0.4 uM of each primer, 100 nM of TaqMan® probe, 100 ng BSA, 4 units of RnaseOUT recombinant inhibitor (Invitrogen) 5.7 uL of water and 2 uL of RNA sample. The reverse transcription and PCR amplification were performed in a single tube on the Light Cycler (Roche) as follows: one cycle of 50° C. for 15 min, one cycle of 95° C. for 2 min followed by 45 cycles of 95° C. for 10 sec, 60° C. for 30 sec. To determine the viral load in each sample, the PCR reactions were monitored by recording the amount of fluorescence emission at each PCR cycle. PCR threshold cycle (Ct) method was used for sample comparison. Standard curves showing plots of Ct values versus Log PFU or genome copy number were obtained by using plasmid DNA or spiked samples with titered virus at a predetermined PFU.

Vaccinations. Six to eight week old female C57Bl/6 mice (National Cancer Institute, Frederick Cancer Research and Development Center, Frederick, Md.) were vaccinated intramuscularly with indicated doses of INA-inactivated, mouse-adapted EBOV diluted in endotoxin-free PBS once or twice at 3-week intervals. Control mice were vaccinated on the same schedule with PBS. Serum samples were obtained from each mouse on days 0 and 28 post vaccination. Mice were challenged 4 weeks after the second vaccination by intraperitoneal injection with 1000 pfu (~30,000 $LD_{50}$) of mouse-adapted EBOV diluted in phosphate buffered saline (PBS) (Bray et al., J. Infect. Dis. 178:651-61 (1998)). After challenge, mice were observed at least twice daily for illness.

Throughout the experiment, mice were housed in microisolator cages and provided autoclaved water and chow ad libitum.

Research was conducted in compliance with the Animal Welfare Act and other federal statutes and regulations relating to animals and experiments involving animals and adhered to principles stated in the *Guide for the Care and Use of Laboratory Animals*, National Research Council, 1996. The facility where this research was conducted is fully accredited by the Association for Assessment and Accreditation of Laboratory Animal Care International.

Antibody titers. Levels of EBOV-specific antibodies were determined, as described by Swenson et al., Vaccine 23:3033-42 (2005). Briefly, the wells were coated with sucrose-purified and γ-irradiated/inactivated EBOV-Zaire. Endpoint titers were established as the inverse of the last dilution where the optical density of the sample was ≧0.2 greater than the corresponding control wells (irrelevant heterologous antigen).

Determination of T cell response to INA-inactivated EBOV by intracellular IFN-γ staining. Splenocytes were isolated and cultured at 37° C. for 5 h in the presence of 1-5 µg of peptide(s) or PMA (25 ng/ml) and ionomycin (1.25 µg/ml) in 100 µl of RPMI-EHAA medium supplemented with 10% heat-inactivated fetal bovine serum, 2 mM glutamine, 10 µg of gentamicin per ml, 5 mM HEPES, human recombinant interleukin (IL)-2 (10 U/ml, National Cancer Institute), and 0.05 mM β-mercaptoethanol medium and containing 10 µg/ml of brefeldin A (Epicentre Technologies, Madison, Wis.). Cells were blocked with Mab to FcRIII/II receptor and stained with anti-CD44 FITC and either anti-CD8 or anti-CD4 Cy-Chrome (Pharmingen, San Diego, Calif.) in staining wash buffer (PBS, 2% fetal bovine serum 0.01% sodium azide, Sigma, St. Louis, Mo.), with brefeldin A (10 µg/ml). The cells were fixed in 1% formaldehyde (Ted Pella, Redding, Calif.), made permeable with staining wash buffer containing 0.5% saponin (Sigma, St. Louis, Mo.), and stained with anti-IFN-γ phycoerythrin (PE) (Pharmingen, San Diego, Calif.). The data were acquired by a FACSCalibur flow cytometer and analyzed with CELLQuest software (Becton-Dickinson Immunocytometry systems, San Jose, Calif.). Samples were considered positive if the percentage of CD8+, CD44+, INF-γ-positive cells was greater than two fold above background. Background was determined by adding an irrelevant peptide from Lassa N (RPLSAGVYMGNLSSQ, SEQ ID NO: 1) or no peptide in a solution that contained equivalent amounts of the dimethylsulfoxide used to dilute peptides.

Electron Microscopy: Live or INA-inactivated EBOV were applied to 300-mesh, nickel electron microscopy grids precoated with formvar and carbon, treated with 1% glutaraldehyde in PBS for 10 min, rinsed in distilled water, and negatively stained with 1% uranyl acetate. For immunoelectron microscopy, viruses were processed as described for fluid specimens (Geisbert et al., Virus Res. 39:129-50 (1995)). Briefly, fractions were applied to grids and immersed for 45 min in dilutions of monoclonal antibodies against EBOV GP. Normal mouse ascetic fluid was tested in parallel. Grids were washed with the TRIS buffer and incubated for 45 min with goat anti-mouse IgG labeled with 10 nm gold spheres (Ted Pella Inc. Redding, Calif.). Grids were washed in PBS, and fixed in 1% glutaraldehyde. After fixation, grids were rinsed in drops of distilled water and negatively stained with 1% uranyl acetate. For pre-embedment staining, cells were stained with anti-Ebola GP mAb followed by gold-anti-mouse Ab, fixed with 2% glutaraldehyde in Millonig's buffer (pH7.4) for 1 h and post-fixed in 1% uranylacetate, dehydrated and embedded in POLY/BED 812 resin (Polysciences, Warrington, Pa.). Resin was allowed to polymerize for 16 h at 60° C., Ultrathin sections (~80 nm) were cut, placed on 200-mesh copper electron microscopy grids and negatively stained. Stained grids were examined with a JEOL 1200 EX transmission electron microscope at 80 kV.

Results

Figure 8A:
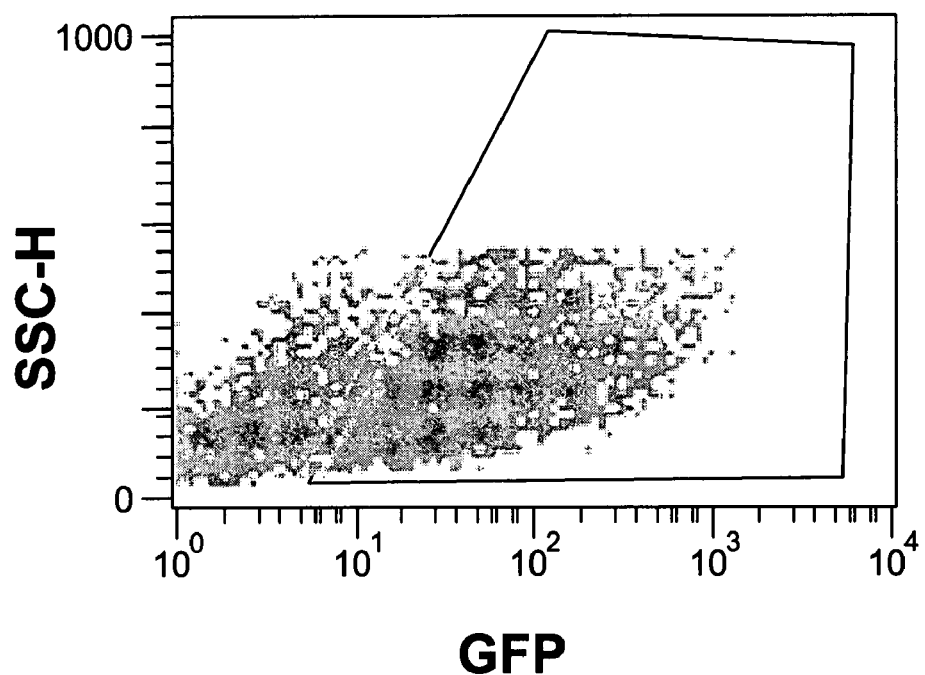
FIG. 8A-B shows that treatment with INA resulted in complete loss of infectivity of Ebola virus. EBOV-GFP was irradiated with UV with (FIG. 8B) and without (FIG. 8A) INA and used to infect Vero-E6 cells. After 96 hours, cells were fixed by 10% buffered formalin and analyzed by flow cytometry for GFP expression as an indicator of infection. While UV alone had no effect on infectivity of the virus (FIG. 8A), UV irradiation of virus pretreated with INA resulted in complete loss of infectivity (FIG. 8B).
Figure 8B:
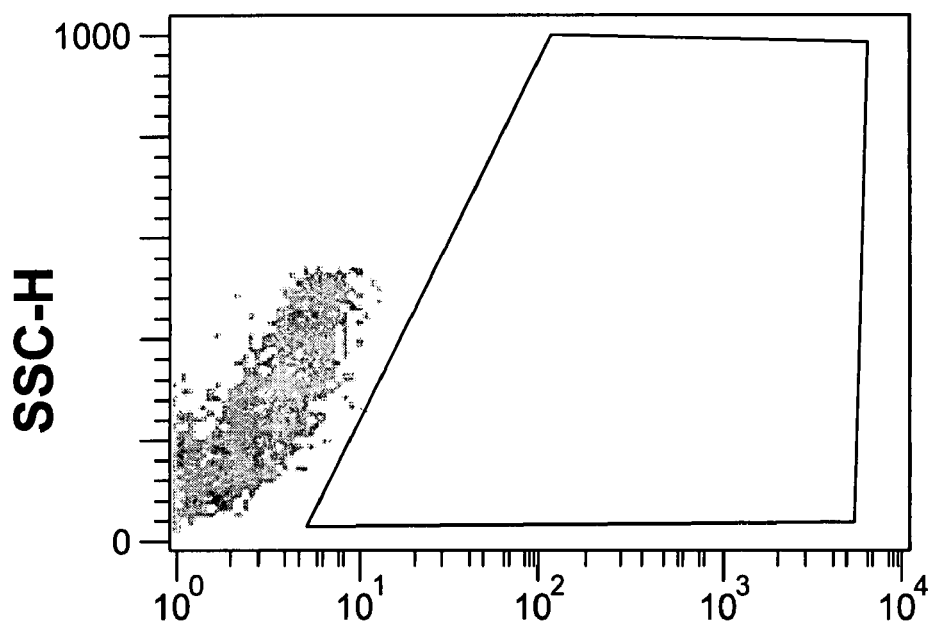

Treatment with INA followed by UV irradiation inactivates EBOV. To examine if EBOV can be inactivated by INA, a recombinant EBOV engineered to express green fluorescent protein (GFP) (Towner et al., Virology 332:20-7 (2005)) was used for initial experiments. EBOV-GFP was treated with 100 µM INA for 30 min at 4° C. Residual INA in the aqueous phase was then inactivated by 20 mM glutathione (reduced form). INA-treated virus was then exposed to far UV light for 10 minutes using a 1 inch water filter to avoid heating of the sample. As control, virus was UV irradiated in the absence of INA. Vero E6 cells were infected with untreated virus, UV treated virus and INA+UV treated virus. The virus infection was visualized by flow cytometry at 24 h, 48 h, 72 h, and 96 h time points. While UV alone had no effect on infectivity of the virus, UV irradiation of virus pretreated with INA resulted in complete loss of infectivity. FIG. 8 shows a representative result from the 96 h time point. Several dose response experiments were also carried out which showed that, depending on the amount of virus, a concentration between 100-200 µM was sufficient to inactivate EBOV completely (data not shown). Maximum concentration of virus used in these experiments was $2 \times 10^6$ pfu/ml.

Figure 9:
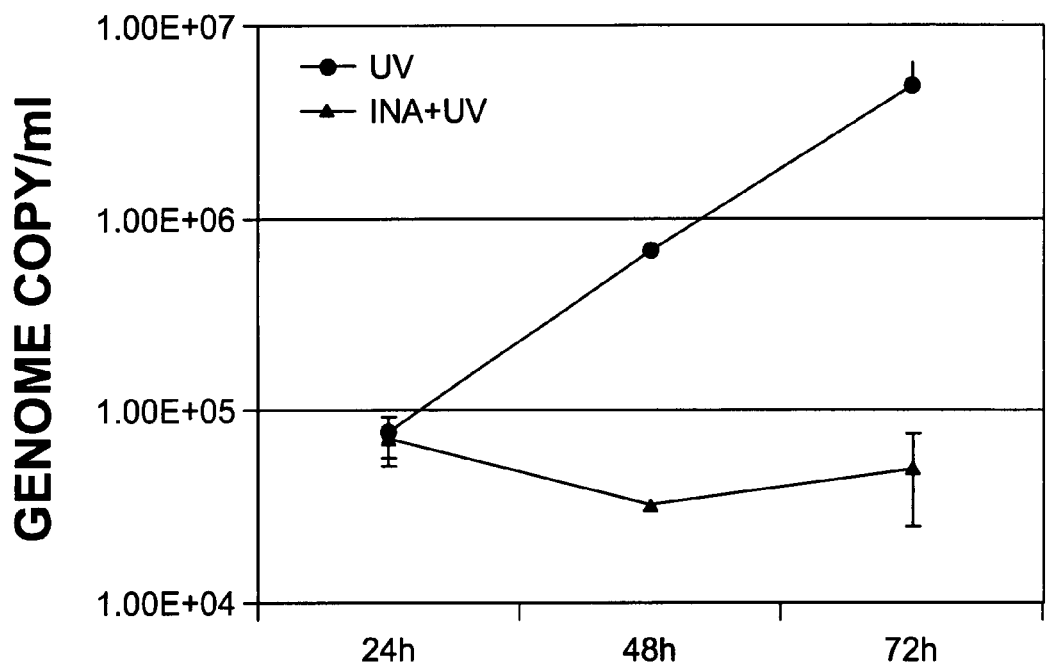
FIG. 9 shows that INA treatment of Ebola viral particles eliminates viral growth in mammalian cells (Vero-E6 cells). Zaire Ebola virus was treated for 10 minutes with UV alone (control) or pretreated with 100 μM INA before UV irradiation. The control and INA inactivated viruses were used to infect Vero E6 cells at an MOI of 10. Virus replication was monitored using a real time PCR assay. Genome copy numbers are shown from triplicate samples.

To ensure that INA treatment can also inactivate the authentic (non-recombinant) virus, Zaire EBOV was treated with UV alone or INA+UV and used to infect Vero E6 cells at an MOI of 10. After infection, cells were incubated in full medium at 37° C. Supernatants were harvested after 24 h, 48 h, or 72 h and viral RNA was purified from the supernatants. Genome copy numbers in the culture supernatants were quantified using a real time PCR (RT-PCR) assay. As shown in FIG. 9, replication of the virus was evident in the control samples as early as 48 h. In contrast, INA inactivated virus did not show any growth over a 72 hour incubation time and the genome copies detected in the culture remained at the level of the initial input.

Figure 10:
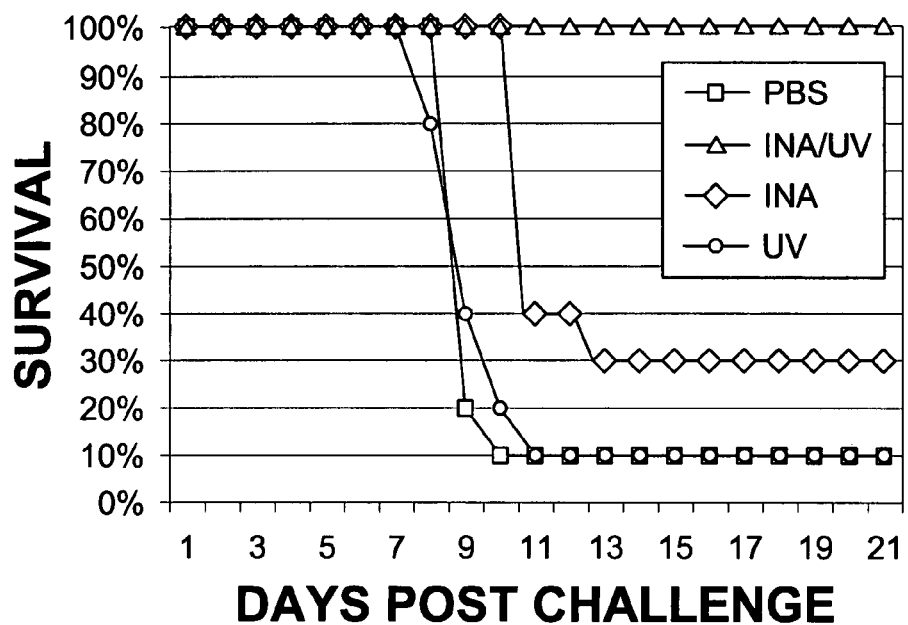
FIG. 10 illustrates that INA-inactivated Ebola virus is not infectious in mice. 1000 Pfu of mouse-adapted EBOV were treated with INA alone, UV alone, or with INA followed by UV and used to infect groups of C57/B16 mice (n=10). Two other control groups were infected with untreated virus diluted in PBS. Survival was monitored over 20 days. As illustrated, 100% survival was observed for mice who received INA-inactivated Ebola virus (triangle symbols). In contrast, only about 10% of mice treated with PBS-treated viruses (squares) and UV-treated viruses survived. Treatment of Ebola viruses with INA alone (diamonds) improved survival slightly.

The lack of infectivity of INA-inactivated EBOV was then tested in a mouse infection model. When mice were infected with a 1000 Pfu of mouse adapted EBOV-Z pretreated with INA+UV all the mice survived the challenge and there was no sign of disease in the mice (FIG. 10, triangles). In contrast, virus treated with INA or UV alone remained lethal (FIG. 10, diamonds and circles). These data clearly demonstrate that INA treatment is an efficient method to abolish the Ebola virus infectivity.

Figure 11A:
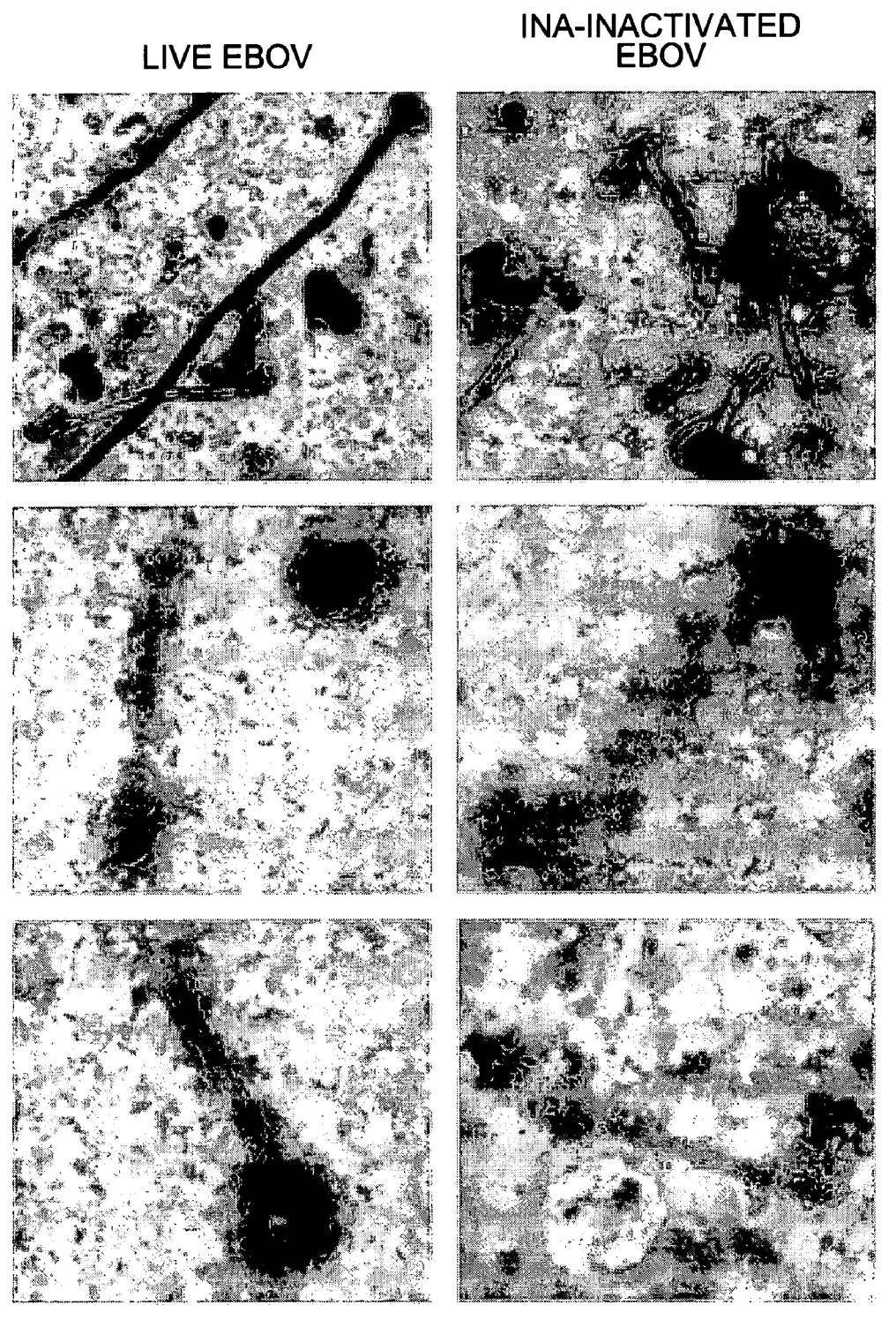

INA-inactivated virus retains its normal morphology and the antibody reactivity of the glycoprotein: Electron microscopy studies were performed to determine if treatment with INA+UV had any effect on the morphology of the virus or the conformational epitopes of GP. As shown in FIG. 11A, INA inactivated virus was morphologically indistinguishable from the live virus. Staining with the anti EBOV GP mAb 13C6, which recognizes a conformational epitope, showed strong staining with both live and INA inactivated virus (FIG. 11A).

Figure 11B:
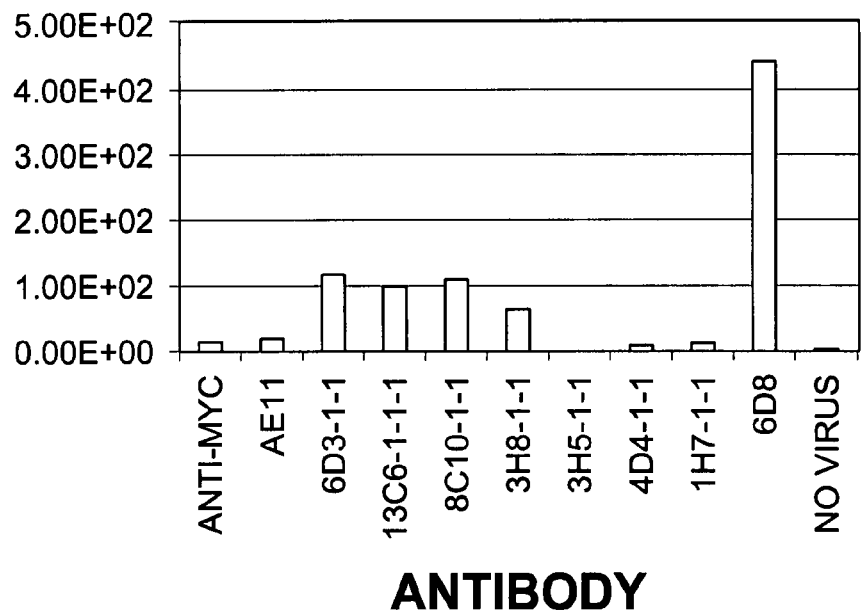
Figure 11B:
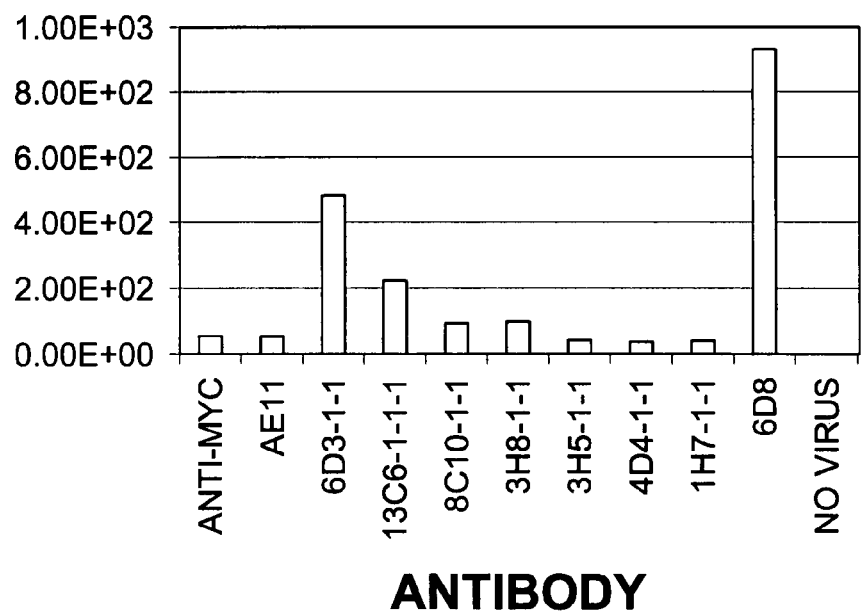

To further examine the question of preservation of conformational epitopes, the binding of live and inactivated EBOV to a panel of anti-GP antibodies was examined using a virus capture assay. Different Monoclonal antibodies against Ebola GP or control antibodies AE11 (anti Ebola VP40) and 9E10 (anti-Myc) were immobilized on 96 well plates. After blocking, $5 \times 10^5$ pfu of live or INA-inactivated EBOV were added to each well and incubated for 1 h. After extensive washing in PBS, the bound viruses were lysed in TRIazol reagent. RNA was prepared and the viral genome was quantified using real time PCR. As shown in FIG. 11B, the antibodies showed a comparable efficiency in capture of the live versus INA-inactivated EBOV. These data suggest that the overall surface conformation of EBOV glycoprotein is not affected by treatment with INA.

Figure 12:
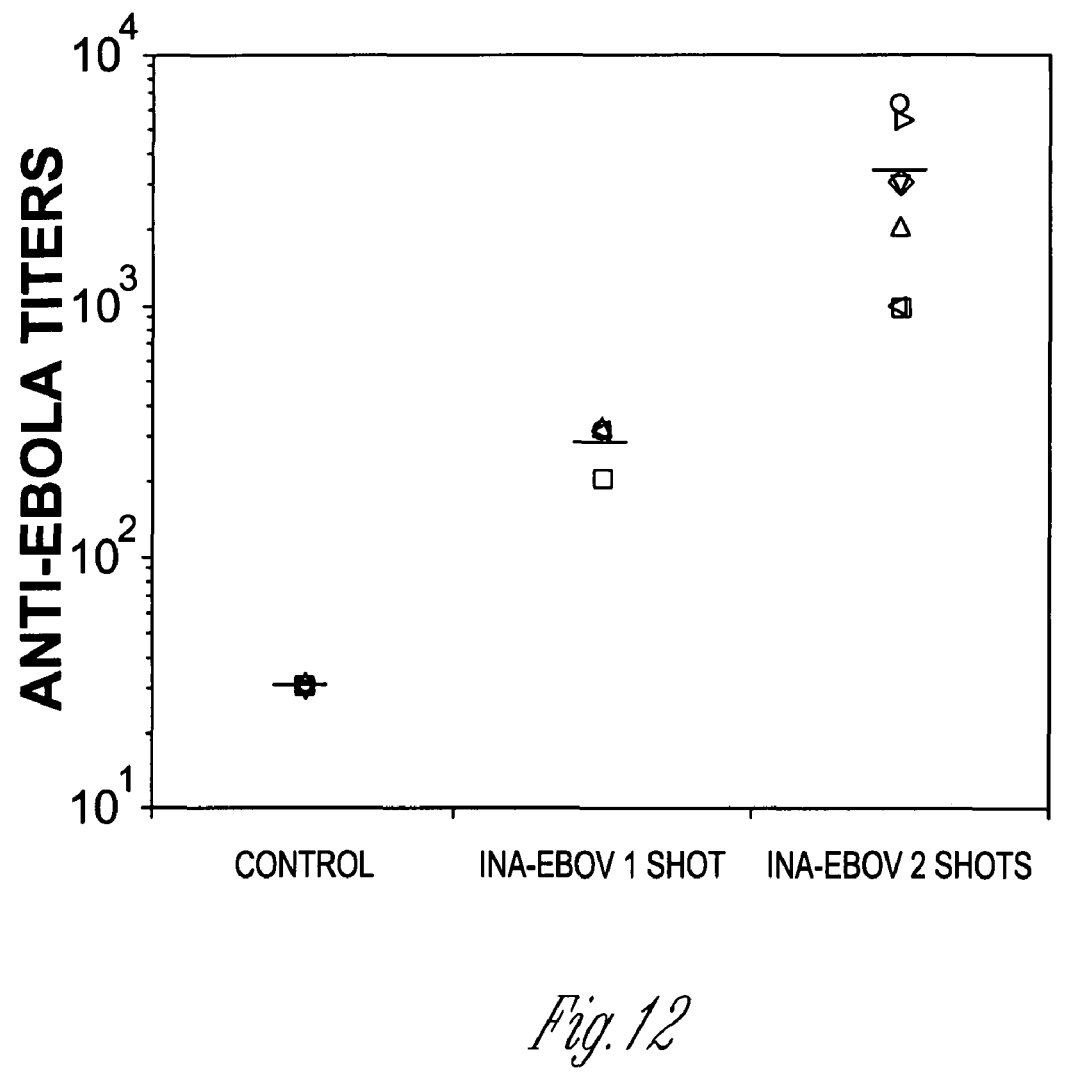

Immunization with INA-inactivated EBOV induces antibody response. To investigate if immunization with INA-inactivated EBOV can confer protective immunity against lethal challenge, groups of mice were immunized with one or two intraperitoneal injections (three weeks apart) of a dose of INA-inactivated EBOV equivalent to $5\times10^4$ Pfu. Two weeks after each vaccination, sera were collected from the mice to measure the antibody response. Anti-EBOV titer was measured by an ELISA using irradiated whole virus as immobilized antigen. As shown in FIG. 12, a single vaccination of the mice resulted in anti-EBOV specific titers of about 1:300. The titer was significantly increased after the second vaccination, reaching an average of 1:3200 (FIG. 12).

Induction of $CD8^+$ T cell responses specific for Ebola epitopes by vaccination with INA-Treated Ebola. As previously described, protective cellular responses can be detected in both C57Bl/6 mice and BALB/c vaccinated mice (Olinger et al., J. Virol. 79:14189-96 (2005)). To investigate if INA-inactivated EBOV can induce specific T cell responses against a range of peptides derived from EBOV proteins were examined using IFNγ intracellular staining as described above in the Materials and Methods section. As shown in Table 2, INA-EBOV vaccinated C57Bl/6 ($H-2^b$) mice displayed CD8+ T-cell responses against ZEBOV GP: WIPYF-GPAAEGIYTE ($GP_{531}$; SEQ ID NO:2), NP epitopes VYQVNNLEEIC ($NP_{44}$; SEQ ID NO:3) and DAVLYY-HMM ($NP_{663}$; SEQ ID NO:4).

TABLE 2

ZEBOV specific cellular responses detected following vaccination.[a]

| Strain | Protein | Epitope | Amino Acid Position | INF-γ ICC[b] |
|---|---|---|---|---|
| C57BL/6 | GP | WIPYFGPAAEGIYTE (SEQ ID NO: 2) | 531-545 | 0.19/0.04 |
| | NP | VYQVNNLEEIC (SEQ ID NO: 3) | 44-52 | 0.14/0.04 |
| | | DAVLYYHMM (SEQ ID NO: 4) | 663-671 | 0.17/0.04 |
| | VP35 | RNIMYDHL (SEQ ID NO: 5) | 225-233 | 0.25/0.04 |
| | VP40 | LRIGNQAFLQEFVLPP (SEQ ID NO: 6) | 150-165 | 0.13/0.04 |
| BALB/c | GP | VSTGTGPGAGDFAFHK (SEQ ID NO: 9) | 141-155 | 0.12/0.03 |
| | VP24 | PGPAKFSLL (SEQ ID NO: 8) | 214-222 | 0.11/0.03 |

[a]Mice vaccinated with INA-inactivated EBOV were assessed ex vivo for cellular responses to previously described ZEBOV epitopes in GP, NP, VP24, VP30, VP35, and VP40 (Olinger et al., J. Virol. 79:14189-96 (2005)). Mice received a booster vaccination on day 14. Splenocytes were collected seven days later.
[b]Splenocytes were used ex vivo for identification of peptides that induced IFN-γ expressing CD8+ T cells. Data shown represent intracellular IFN-γ data after a 5-h re-stimulation with peptide. The data are expressed as the peptide-induced % positive/background % positive.

The strongest response detected was to the VP35 epitope RNIMYDHL ($VP35_{225}$; SEQ ID NO:5). Lastly a response to the VP40 epitope LRIGNQAFLQEFVLPP ($VP40_{150}$; SEQ ID NO:6) was detected in vaccinated mice.

BALB/c mice had detectable CD8+ T-cell responses to two of the ZEBOV peptides derived from GP and VP24 (Table 2). A CD8+ response to the NP peptide sequence, SFKAALSSL ($NP_{279}$; SEQ ID NO:7) was detected as well as the VP24 epitope PGPAKFSLL (SEQ ID NO:8)(Table 2). Combined, these data indicate that vaccination with INA-inactivated induces cellular immune responses.

Figures 13A, 13B:
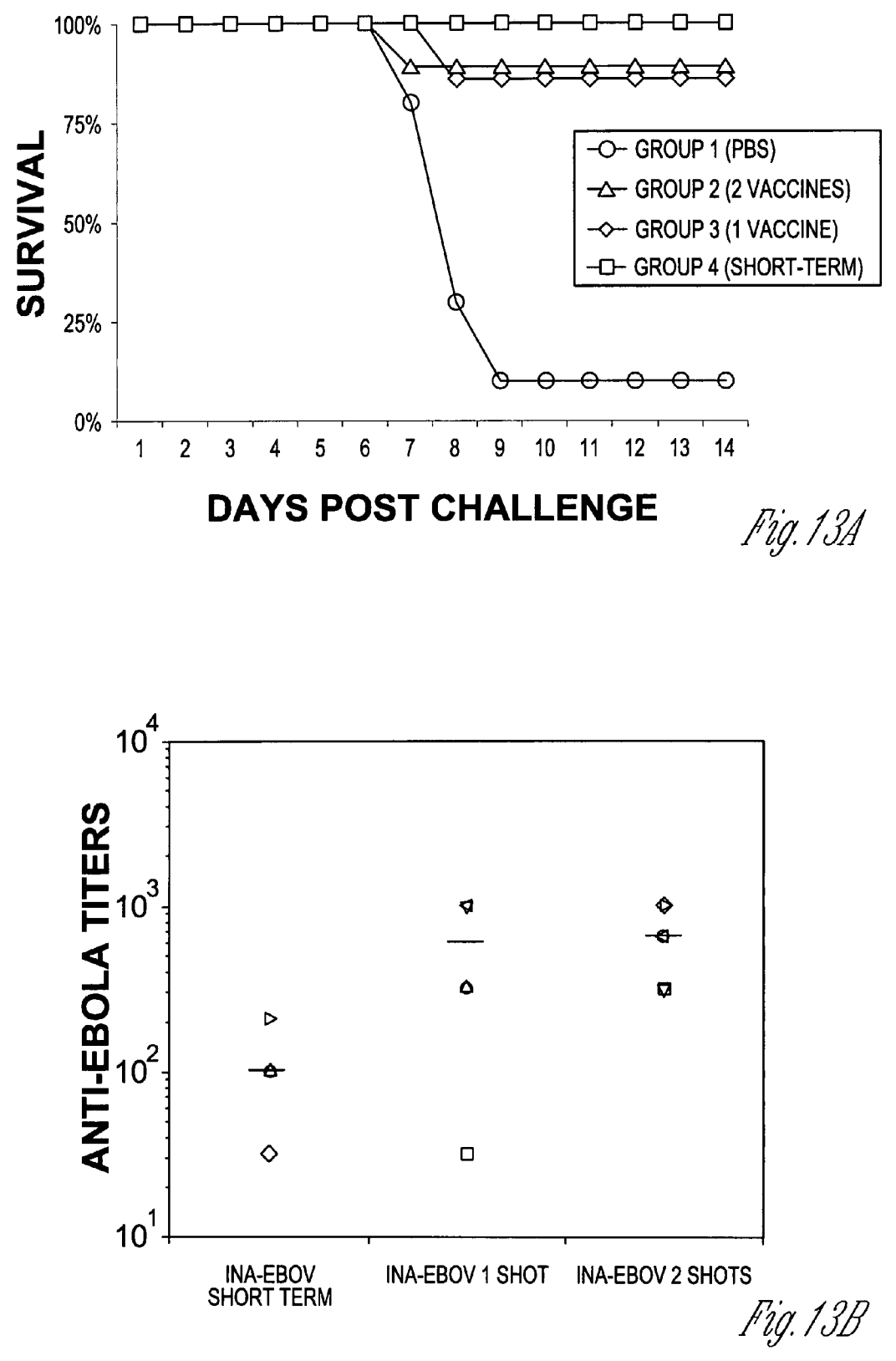

Vaccination with INA-inactivated EBOV protects against lethal Ebola infection. INA-inactivated virus was then used in a vaccination study to evaluate its vaccine potential. Groups of mice were immunized either once or twice at a 2 week interval with 50000 Pfu of INA-inactivated mouse adapted EBOV-Z. Three weeks after the last immunization mice were challenged with 1000 pfu of mouse adapted EBOV-Z. As shown in FIG. 13A, vaccination with one or two doses of INA-inactivated virus in the absence of adjuvant conferred over 80% protection from lethal challenge.

We had previously demonstrated that inoculation of mice with Ebola virus-like particles conveys short term protection against a lethal challenge, an effect primarily conveyed by activation of natural killer cells (Warfield et al., J Exp Med 200:169-79 (2004)). In contrast, irradiated virus is unable to provide such short term protection (id.). To examine if INA-inactivated EBOV can induce a protective innate immune response, mice were injected intraperitoneally with 50000 Pfu of INA-inactivated mouse adapted EBOV-Z or PBS as control and challenged with 1000 pfu of mouse adapted EBOV-Z three days later. All the mice treated with INA-inactivated virus survived the infection while all the control mice succumbed to death (FIG. 13A).

Antibody titers in these animals were also determined after challenge by ELISA using inactivated EBOV as antigen. As shown in FIG. 13B, after viral challenge the titers were found to be 1-2 orders of magnitude higher than the pre-challenge titers (FIG. 12). Interestingly, the short term vaccinated mice also showed strong antibody response post challenge suggesting that the virus was not entirely cleared by the innate response, but rather the activation of the innate response resulted in mounting a protective adaptive response.

Taken together, these data indicate that INA is an effective inactivation agent for use in preparing immune system-stimulating compositions of hemorrhagic fever viruses such as Ebola virus.

EXAMPLE 6

Administration of INA-Treated Influenza Viruses Protects Animals from Influenza Infection This Example illustrates that INA-inactivated influenza viruses can be used to immunize animals against death by the disease it causes.

Materials and Methods

Purified influenza virus strain H3N2 was prepared by and obtained from Charles River Laboratories (N. Franklin Conn.). 1,5 Iodonaphthylazide (INA) was synthesized and supplied by "Combinix" Inc. (San Mateo Calif.). 3,3'-dioctadecyloxacarbocyanine perchlorate (DiO), chloromethylfluorescein diacetate (CMFDA) and Amplex Red Neuraminidase assay kit were from Invitrogen-Molecular Probes (Carlsbad, Calif.). PKH-67 and PKH-26 were from Sigma. 3-1 KB Carcinoma cell line was generously supplied by Suresh Ambudkar from the laboratory of Cell Biology, NCI/NIH. CD4-GFP construct was a generous gift from W. Popik from the Oncology Center, The Johns Hopkins University School of Medicine Baltimore, Md.

Inactivation of Influenza Virus: Inactivation of Influenza virus by INA was carried out essentially as described for retroviruses (Example 1). In short, band purified H3N2 influenza virus was suspended in PBS at a concentration of 1 mg/ml protein. INA from a 40 mM stock solution in DMSO was added to the virus suspension in several installments and thoroughly mixed. The virus was incubated for 15 minutes in the dark and irradiated with UV light using a 100 W mercury lamp source for 2 minutes as described above.

In vitro infectivity and neuraminidase activity: Purified influenza virus strain H3N2 (X-31) at a protein concentration of 1 mg/ml was treated with different concentrations of INA and then inactivated by UV irradiation using the protocol described above and in Raviv, Y. et al. (J. Virol 79, pp. 12394-12400 (2005)) for the inactivation of HIV. The INA-treated viral preparation was then divided into two experimental groups. One INA-treated viral group was subjected to an infectivity assay and the second INA-treated viral group was tested for neuraminidase activity.

To monitor infection the binding of red blood cells to influenza virus-infected cells as assessed as described by Puri et al., J. Virol. 64: 3824-3832 (1990). Duplicate 25 pg aliquots of the virus in DMEM medium+2% bovine serum was added to KB carcinoma cells grown to confluence in 6 well plates. The virus-cell mixture was incubated for 2-3 hours at 37° C. and then the cells were washed and further incubated with fresh DMEM+10% bovine serum over night at the same temperature. The cells were washed again and labeled with the cytosolic fluorescent probe CMFDA (5-chloromethylfluorescein diacetate; Excitation wavelength 485 nm; Emission wavelength 525 nm) by following the manufacturer protocol (Molecular Probes). The cells were then washed with PBS and incubated with a suspension of 0.5% human erythrocytes pre-labeled with the fluorescent membrane probe PKH-26 (Excitation wavelength 530 nm; Emission wavelength 580 nm) (Sigma). After 15 minutes incubation at room temperature the cells were washed with PBS five times and lysed with a solution of 1% Triton X-100. The fluorescence values of PKH26/CMFDA at 580/525 nm were measured using a "Cytofluor" fluorescent plate reader.

Neuraminidase activity was determined by measuring the hydrogen peroxide induced fluorescence of a fluorescent probe using the "Amplex Red" neuraminidase assay kit (Molecular Probes) following the manufacturer's protocol.

As a control, non-infected cells were incubated with PKH labeled erythrocytes. Background levels of fluorescence were determined from the signal obtained by incubating labeled erythrocytes in wells without cells. The signal from the non-infected cells was not significantly different from background.

Influenza viral-cell fusion assay by photosensitized labeling: Fusion by photosensitized labeling was measured as described by Pak et al. J. Biol. Chem. 269: 14614-14619 (1994) and Raviv et al., Virology, 293: 243-251 (2002), using human erythrocyte resealed ghosts (1 ml) that were labeled with the fluorescent membrane probe PKH67 (Sigma) and incubated with 20 μCi $^{125}$INA for 15 minutes on ice. The ghosts were washed and divided into 5 experimental groups. Influenza virus at 1 mg/ml protein was treated with different concentration of INA and irradiated as described above. The virus was mixed with the resealed ghosts for 30 minutes at room temperature, washed, and then the appropriate amount of citric acid was added to the mixture to lower the pH to pH 5.0. The tubes were further incubated at 37° C. for 15 minutes, the viral/erythrocyte ghost mixture was then irradiated at 488 nm for 30 seconds using an argon laser at the intensity of 0.5 W. The ghosts were lysed and the hemagglutinin (HA) was isolated by immunoprecipitation, then the immunoprecipitated proteins were separated by SDS-PAGE. The radioactivity incorporated in the HA molecules was measured by autoradiography using a phosphorimmager.

The controls employed were untreated virus (100%) and untreated virus that was bound to the ghosts and kept at neutral pH 7.4 (signal=0) so that fusion was not triggered by adjustment of the pH to 5.0.

Measurement of lipid mixing by fluorescence dequenching: Labeling of virus with octadecyl rhodamine (R18) and fusion with RBC ghosts were performed as described by Claque et al., Biochemistry. 30: 5491-5497 (1991); Pak et al., J. Biol. Chem. 269: 14614-14619 (1994); Puri et al., J. Virol. 64: 3824-3832 (1990). Influenza virus was inactivated with 100 μM INA as described and labeled with R18. The R18-labeled virus was prebound to RBC resealed ghosts at room temperature for 20 min and washed. The sample was transferred to a cuvette in the fluorimeter at 37° C. and the pH was lowered to 5.0 by adding citric acid. Fluorescence was monitored before and after the addition of the citric acid. Percent fluorescence dequenching was determined as $100\times[(F-Fo)/(Ft-Fo)$, where Fo and F are fluorescence intensities at time zero and at a given time point, respectively, and Ft is the total fluorescence obtained after disruption of cells by Triton X-100. As a control for non-specific dequenching the virus was inactivated by pre-exposure to pH 5.0 followed by incubation with cells at pH 7.4 (Korte et al., J. Virol. 73: 4567-4574 (1999).

Fluorescence recovery after photobleaching (FRAP) acquisition and analysis: FRAP was performed using a Zeiss LSM 510 (Carl Zeiss, Jena, Germany) confocal laser scanning microscope. HeLa cells were plated on 35 mm glass bottom dishes (MatTek, Ashland, Mass.) and either transfected with CD4-GFP 24 hours prior to confocal analysis as described previously (24) or labeled with DiO one hour prior to the FRAP analysis. INA was added to the cells from stock of 30 mM in dimethyl sulfoxide (DMSO) to a final concentration of 20 or 100 μM. After 10 minutes incubation at room temperature, the sample was irradiated with UV light at 10 mW/cm$^2$ for two minutes. The cells were then submitted to FRAP while kept at physiological conditions of 37° C. and 5% $CO_2$ in a stage incubation system (Incubator S; PeCon GmbH, Erbach, Germany). A 488 nm $Ar^+$ laser line was used for excitation and emission light was collected with a 500-550 bandpass filter. A 40X/1.3 NA oil immersion objective lens was used with a zoom factor of 4. The detector pinhole was opened slightly to acquire an optical section of 2 μm thickness. This allowed more light to be collected for better quantification. Three pre-bleach images were acquired to determine the rate of non-purposeful photobleaching. Photobleaching was performed by increasing the transmission of the laser to 100% for 20-50 iterations to optimize the extent of bleaching. Following photobleaching 8-10 images were acquired at one second intervals and then the acquisition rate was changed to ten second intervals to follow the recovery to completion. A total of 20-40 images were acquired. FRAP analysis was performed using the MIPAV (CIT/NIH, Bethesda, Md.) software package using a 1D diffusion FRAP model to retrieve the mobile fraction (Lippincott-Schwartz et al., Nat Rev Mol Cell Biol. 6: 444-456 (2001)). Data were automatically corrected with background subtraction, as well as normalization for the non-purposeful photobleaching rate calculated from the whole cell membrane.

Electron microscopy: Electron microscopy was carried out essentially as previously described for retroviruses (Raviv et al., Journal of Virology. 79: 12394-12400 (2005)). In short live or INA-inactivated influenza viruses were applied to 300-mesh, nickel electron microscopy grids pre-coated with formvar and carbon, treated with 1% glutaraldehyde in PBS for 10 min, rinsed in distilled water, and negatively stained with 1% uranyl acetate. Stained grids were examined with a JEOL 1200 EX transmission electron microscope at 80 kV.

Protective Immunization Studies: To assess the ability of INA-inactivated influenza virus to induce protective heterosubtypic immunity, mice were vaccinated just once with live A/Aichi/68 X-31 (X31, H3N2), INA-treated X31, or B/Ann Arbor (B/AA) influenza virus. Five week old, female BALB/c mice (Harlan) were acclimated for 3 weeks. Animals were bled by tail vein nick, and 6 days later were anesthetized via intraperitoneal (i.p.) injection of Avertin. The animals were then immunized or infected with 30 µl solution as indicated in Table 3 and described below. As negative controls, mice were given PBS (naïve) or infected with influenza B/AA intranasally. B/AA influenza was used as a non-specific viral infection control. As positive controls, mice were infected intranasally with live X31. The first experimental group consisted of mice immunized with INA-treated X31 delivered subcutaneously, the standard route of immunization for traditional influenza vaccines. The second experimental group was comprised of animals immunized intranasally with INA-treated X31, with the expectation that this route of delivery would induce a potent mucosal immune response that would provide protection against lethal, heterosubtypic challenge.

The immunization protocols utilized are summarized in Table 3.

TABLE 3

| Group | N | Immunization with | Delivery | Dose |
|---|---|---|---|---|
| A | 10 | PBS | Intranasal | Na |
| B | 8 | B/AA | Intranasal | 1:1000 |
| C | 8 | INA-X31 | Intranasal | 15 µg |
| D | 9 | INA-X31 | Subcutaneous | 15 µg |
| E | 10 | X-31 | Intranasal | 15 µg |

After immunization/infection, the mice were allowed to rest for 4 weeks and then bled to provide serum for determining antibody responses. One week later, all groups of mice were anesthetized and challenged intranasally with 10 $LD_{50}$ of influenza A/PR/8/34 (PR8) in 50 µl volume. The mice were then monitored daily for mortality and weighed every 2-3 days until all animals had either succumbed to infection or recovered most of their initial body weight.

Results

INA reduced influenza viral infectivity without affecting neuraminidase activity: Influenza infectivity is facilitated by viral hemagglutinin (HA) which is an integral membrane protein of the viral envelope whose transmembrane segment's integrity is essential for full fusion and infectivity. Neuraminidase is also an integral membrane protein of the viral envelope only that its catalytic site is located on the hydrophilic segment that protrudes outside the membrane.

Figure 14:
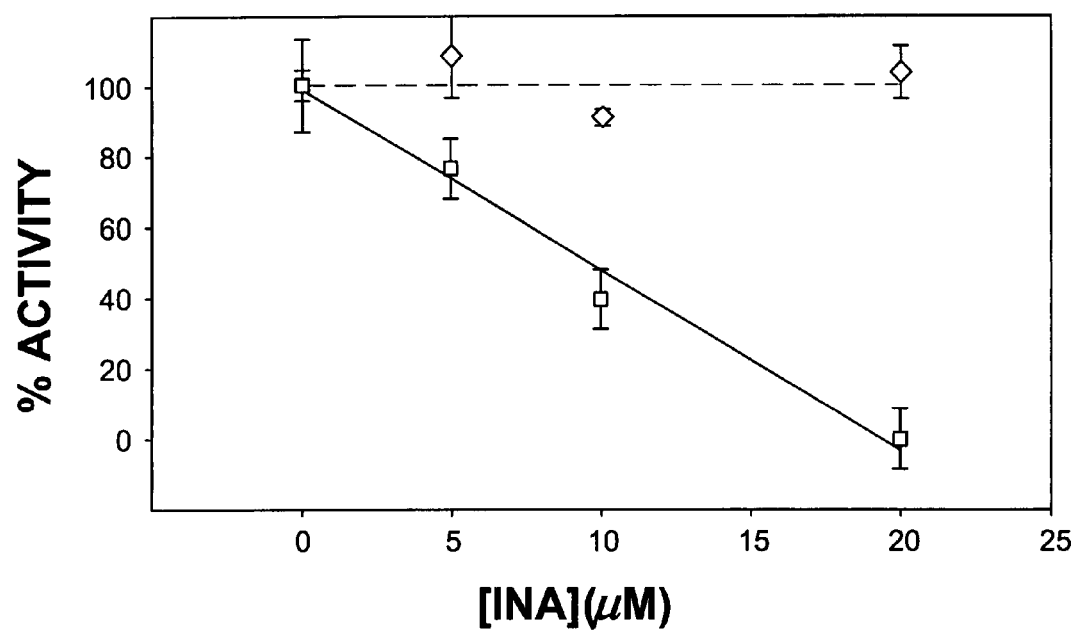
FIG. 14 illustrates the effect of INA on influenza virus. Band purified H3N2 influenza virus was treated with INA at the indicated concentrations. Infectivity and neuraminidase activity was measured as described in Example 6. The square symbols show the infectivity of the influenza virus. The diamond symbols represent the neuraminidase activity of the influenza virus. Data points represent standard deviation from triplicate measurements.

INA treatment of influenza reduced the infectivity of the influenza virus to zero in a dose-dependent manner while the catalytic activity of the viral envelope enzyme neuraminidase was not affected (FIG. 14). Infectivity is facilitated by the fusion protein of influenza virus hemagglutinin (HA) which is an integral membrane protein of the viral envelope whose transmembrane segment's integrity is essential for full fusion and infectivity of the virus (Earp et al., C. T. M. I. 285: 25-66 (2004). Neuraminidase is also an integral membrane protein of the viral envelope only that its catalytic site is located on the hydrophilic segment that protrudes outside the membrane.

Figure 15A:
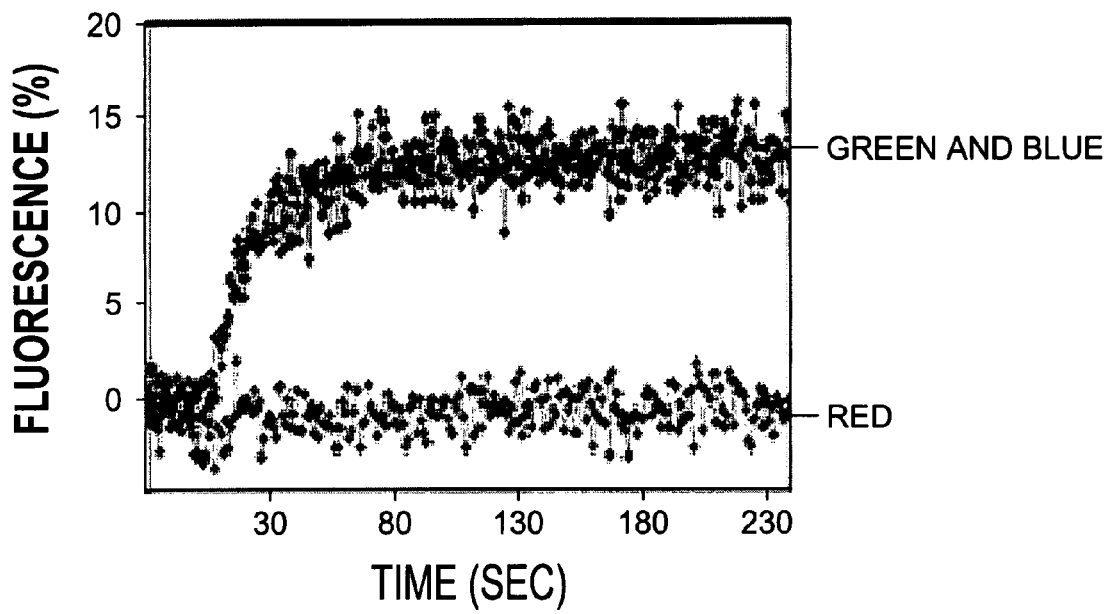
FIG. 15A-B shows that INA has no effect on HA induced lipid mixing. R-18 labeled influenza virus was bound to erythrocytes and fusion was triggered by lowering the pH of the buffer as described in Example 6. Results represent redistribution of viral envelope lipids into the target red cells membrane as measured by R-18 dequenching. Dequenching was measured by the increase in fluorescence of R-18 observed with time after lowering the pH to 5.0. The data are presented as the percentage of the maximal fluorescence observed upon lysis of the viral membrane in 1% Triton-X-100.
Figure 15B:
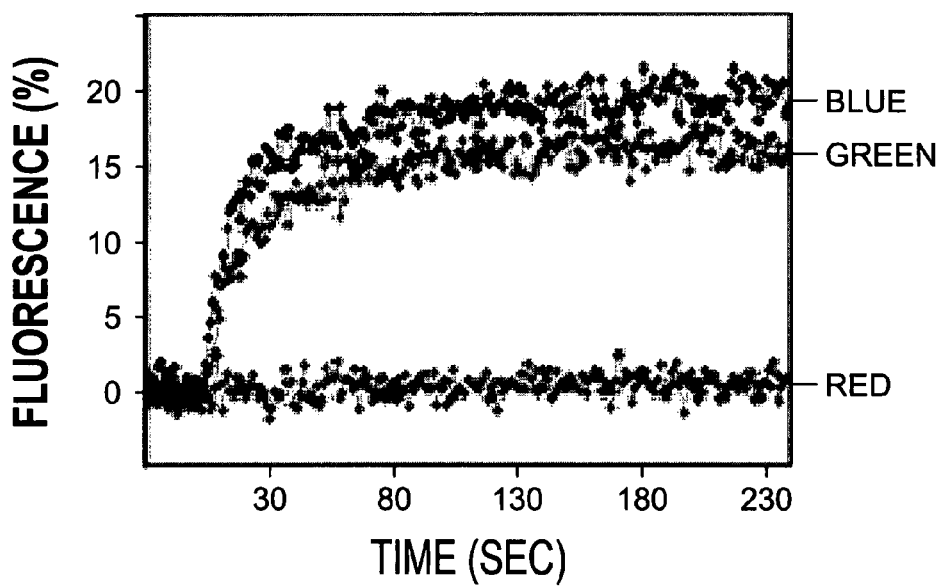

In order to test if the INA effects the ability of the virus to fuse with the target cell membrane, fusion was measured directly by two different methods: Dequenching of R-18 and photosensitized labeling. Dequenching measures the pH dependent mixing of lipids from the viral envelope with lipids of the target cell and this function was not affected by INA relative to non-treated viruses (FIG. 15). Similar results were obtained when the dequenching experiments were repeated using the non-exchangeable fluorescent lipid analogue PKH-26 instead of R-18. When influenza virus is exposed to low pH at 37° C. prior to the mixing with the target cells, its fusion activity is inactivated. The ability of HA to mediate lipid mixing is regarded as a manifestation of the conformational change that the HA molecules undergo in response to low pH (Blumenthal et al., Membrane Fusion. Chem. Rev. 103: 53-69 (1993)). The data shown in FIG. 15 indicate that the conformational transitions of HA are not affected by INA as both INA treated and non treated viruses are equally inactivated by pre exposure to low pH at 37° C. but not at 4° C. Photosensitized labeling, on the other hand, monitors fusion by measuring the pH dependent redistribution of proteins from the viral envelope into the target cell membrane.

Figure 16:
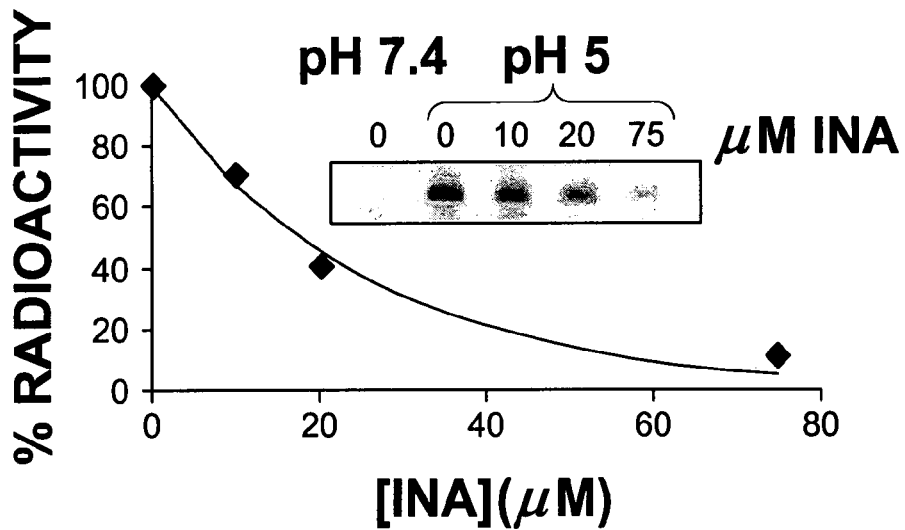
FIG. 16 shows that INA blocks fusion driven insertion and redistribution of viral envelope proteins into the target cell membrane. Insertion of viral envelope proteins was measured by photosensitized labeling by following the extent of $^{125}$INA incorporation into influenza HA after the triggering of cellular fusion at pH 5.0. The experiment was repeated for every indicated concentration of INA. Values represent radioactivity of HA as measured by phosphorimmager enhanced autoradiography. The insert shows the actual labeling of HA as observed by the phosphorimmager. The lane labeled pH 7.4 indicates the measurement was obtained at neutral pH.

FIG. 16 shows that treatment of virus with INA blocked the redistribution of viral envelope proteins into the cell membrane in a dose dependent manner with almost no detectable signal at 100 uM INA. At this concentration the viral envelope proteins did not incorporate into the target cell membrane upon lowering the pH and remained in a position similar to where they were before the onset of fusion at neutral pH.

Figure 17:
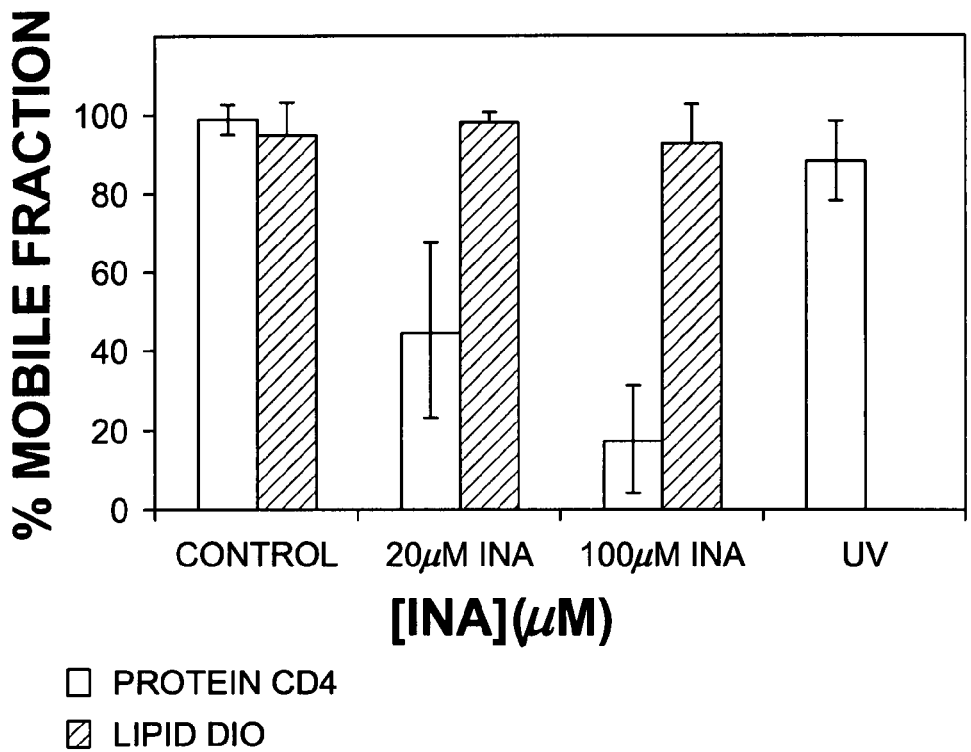
FIG. 17 shows that INA treatment blocks the mobility of proteins but not of lipids in the cell membranes. Translational diffusion of lipids was measured by FRAP as described in Example 6 after treatment with the indicated INA concentrations. The values are presented as the mobile fraction. The fluorescent lipid probe was DiO and the protein probe was GFP-CD4. White bars: Protein. Black bars: Lipid. UV: Control cells irradiated with UV in the absence of INA.

These results suggest that INA may have a general effect on the translational mobility of proteins in the membrane. To test this hypothesis the diffusion of proteins and lipids in the HeLa cell membrane was measured after INA treatment by fluorescence recovery after photobleaching (FRAP). For these experiments CD4 conjugated to GFP (CD4-GFP) was used as the fluorescently-labeled transmembrane protein and DiO as the lipid fluorescent probe. The results presented in FIG. 17 show that the protein mobile fraction was reduced to background level after treatment with INA whereas the mobile fraction of the lipid was not affected.

It was also established visually that the influenza virus maintains its structural integrity after INA treatment. For that purpose, INA inactivated and control viruses were subjected to negative staining and visualized by an electron microscope at low resolution. After examining ten different EM imaging fields for each type of virus the INA inactivated and control viruses appeared indistinguishable and structurally intact (data not shown). All experiments were repeated three times except for the photosensitized labeling that was repeated twice.

INA treatment protects animals against influenza infection and death: ELISA assays at day 28 post-vaccination showed that serum antibody titers specific for X31 were equivalent in mice receiving either live or INA-treated X31. These results indicate that the INA inactivation procedure did not reduce influenza viral antigenicity.

Figure 18:
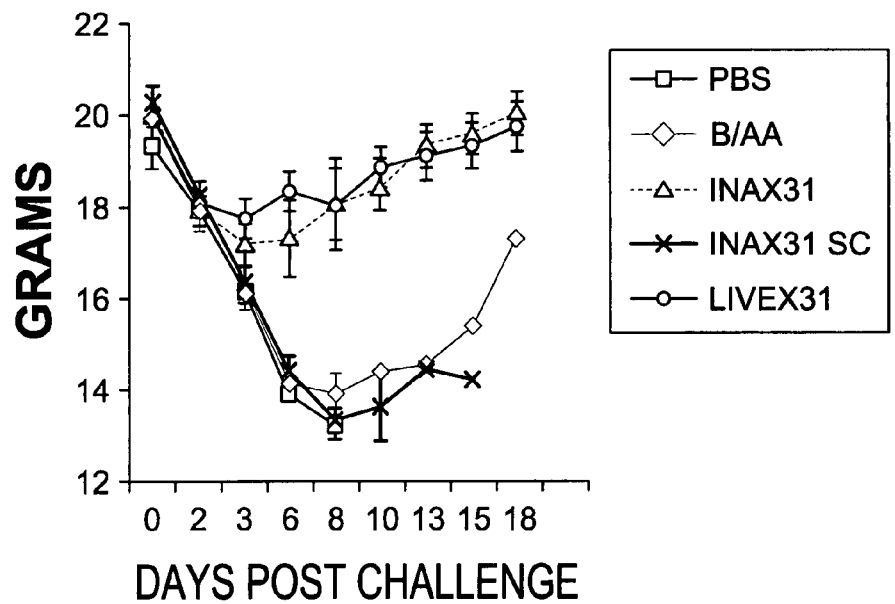
FIG. 18 graphically illustrates the body weight in grams of mice as a function of time after intranasal challenge with 10 $LD_{50}$ of a different influenza virus (A/PR/8, H1N1) than that with which the animals were immunized. As shown, the PBS (□), B/AA (◇) and INA-X31 (subcutaneously, x) pre-immunized animals lost significant weight over a period of about 8 to 10 days. While the B/AA (◇) immunized animals began to recover body weight after about 8 days, the PBS (□) and INA-X31 (subcutaneously, x) immunized animals died after about 8 and 15 days, respectively. In contrast, animals pre-immunized with INA-X31 (intranasal, triangles) or live X31 influenza virus lost very little weight and quickly began to recover the lost weight within about 5-6 days.
Figure 19:
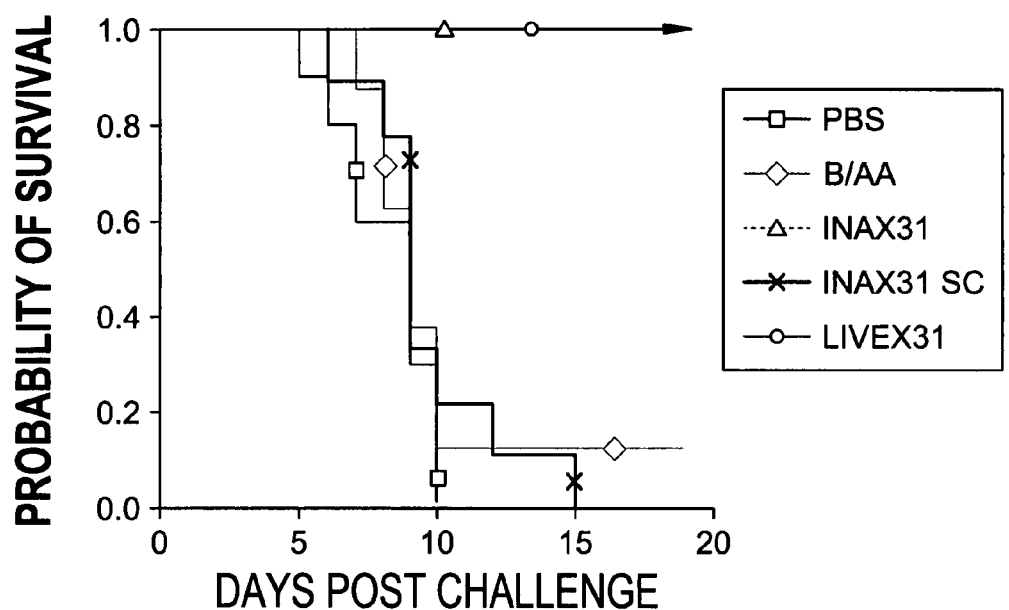
FIG. 19 graphically illustrates the probability of survival of mice as a function of time after intranasal challenge with 10 $LD_{50}$ of live influenza virus (A/PR/8, H1N1). As shown, the PBS (squares) and INA-X31 (subcutaneous, X) immunized animal had no probability of survival after about 10-15 days, and the B/AA immunized animals (diamonds) had a very low probability of survival (0.1) after about 15-20 days. In contrast, animals pre-immunized with INA-X31 (intranasal, triangles) or live X31 influenza virus (circles) had 100% probability of survival after challenge with live influenza virus ($P \leq 0.001$ (log-rank)).

Moreover, when challenged intranasally with 10 $LD_{50}$ of heterologous influenza virus (A/PR/8, H1N1), these live or INA-treated X31 nasally immunized animals exhibited minimal weight loss and 100% survived (FIG. 18-19). In contrast, unvaccinated animals and animals immunized with B/Ann Arbor lost almost one-third of their body weight and almost all animals died after about 6-15 days (FIG. 18-19). Nasal immunization was significantly more effective than subcutaneous immunization—all INA-treated X31 nasally immunized animals exhibited minimal weight loss and 100% survival, but the INA-treated X31 subcutaneously immunized animals exhibited significant weight loss and none survived past fifteen days post-infection (FIGS. 18 and 19).

These results demonstrate that INA-treatment of influenza virus generates an effective vaccine composition that, when administered to mammals, protects those mammals against influenza virus infection and the symptoms associated with influenza infection.

REFERENCES

Arthur et al. (1998). Chemical inactivation of retroviral infectivity by targeting nucleocapsid protein zinc fingers: A candidate SIV vaccine. AIDS Res. Hum. Retroviruses 14 (Suppl. 3), S311-S319.

Arthur et al. (1992). Cellular proteins bound to immunodeficiency viruses: Implications for pathogenesis and vaccines. Science 258, 1935-1938.

Benveniste et al. (1990). Characterization of clones of HIV-1 infected HuT 78 cells defective in gag gene processing and of SIV clones producing large amounts of envelope glycoprotein. J. Med. Prima 19, 351-366.

Bercovici, T, and Gitler, C. (1978). [$^{125}$I]Iodonaphthyl azide, a reagent to determine the penetration of proteins into the lipid bilayer of biological membranes. Biochemistry 17: 1484-89.

Berger, E. A, Murphy, P. M., and Farber, J M. (1999). Chemokine receptors as HIV-1 coreceptors: Roles in viral entry, tropism, and disease. Annu. Rev. Immunol., 657-700.

Bess et al. (1997). Microvesicles are a source of contaminating cellular proteins found in purified HIV-1 preparations. Virology 230, 134-144.

Chan, D. C., Chutkowski, C. T, and Kim, P. S. (1998). Evidence that a prominent cavity in the coiled coil of HIV type 1 gp41 is an attractive drug target. Proc. Natl. Acad. Sci. USA 95: 15613-17.

Chan, D. C., Fass, D., Berger, J M., and Kim, P. S. (1997). Core structure of gp41 from the HIV envelope glycoprotein. Cell 89: 263-273.

Chan, D. C., and Kim, P. S. (1998). HIV entry and its inhibition. Cell 93: 681-684.

Chen, C. H., Matthews, T. J., McDanal, C. B., Bolognesi, D. P., and Greenberg, M. L. (1995). A molecular clasp in the human immunodeficiency virus (HIV) type 1 TM protein determines the anti-HIV activity of gp41 derivatives: Implication for viral fusion. J. Viral. 69: 3771-3777.

Chen, Z., Gettie, A, Ho, D. D., and Marx, P. A (1998). Primary SIVsm isolates use the CCR5 coreceptor from sooty mangabeys naturally infected in west Africa: A comparison of coreceptor usage of primary SIVsm, HIV-2, and SIVmac. Virology 246, 113-124.

Dimitrov, D. S. (2000). Cell biology of virus entry. Cell 101, 697-702.

Dimitrov, D. S., Willey, R., Martin, M., and Blumenthal, R. (1992). Kinetics of HIV-1 interactions with sCD4 and CD4+ cells: Implications for inhibition of virus infection and initial steps of virus entry into cells. Virology 187, 398-406.

Doms, R. W (2000). Beyond receptor expression: The influence of receptor conformation, density, and affinity in HIV-1 infection. Virology 276, 229-237.

Duzgunes, N., Larsen, C. E., Konopka, K., Alford, D. R., Young, L. J., McGraw, T. P., Davis, B. R., Nir, S., and Jennings, M. (1991). Fusion of HIV-1 and SIVmac with liposomes and modulation of HIV-1 infectivity. Adv. Exp. Med. Biol. 300, 167-189.

Frey, S., Marsh, M., Gunther, S., Pelchen-Matthews, A, Stephens, P., Ortlepp, S., and Stegmann, T (1995). Temperature dependence of cell-cell fusion induced by the envelope glycoprotein of human immunodeficiency virus type 1. J. Virol., 1462-72.

Furuta, R. A., Wild, C. T, Weng, Y, and Weiss, C. D. (1998). Capture of an early fusion-active conformation of HIV-1 gp41. Nat. Struct. Biol. 5: 276-279.

Gallo, S. A., Puri, A, and Blumenthal, R. (2001). HIV-1 gp41 six-helix bundle formation occurs rapidly after the engagement of gp120 by CXCR4 in the HIV-1 Env-mediated fusion process. Biochemistry 40:12231-12236.

Hoekstra, D., de Boer, T, Klappe, K., and Wilschut, J (1984). Fluorescence method for measuring the kinetics of fusion between biological membranes. Biochemistry 23, 5675-5681.

Hug, P., Lin, H. M., Korte, T, Xiao, X., Dimitrov, D. S., Wang, J M., Puri, and Blumenthal, R. (2000). Glycosphingolipids promote entry of a broad range of human immunodeficiency virus type 1 isolates into cell lines expressing CD4, CXCR4, and/or CCR5. J. Virol., 74: 6377-6385.

Jernigan, K. M, Blumenthal, R., and Puri, A (2000). Varying effects of temperature, Ca(2+) and cytochalasin on fusion activity mediated by human immunodeficiency virus type 1 and type 2 glycoproteins. FEBS Lett. 474, 246-251.

Jiang, S., Lin, K., Strick, N., and Neurath, A R. (1993). Inhibition of HIV-1 infection by a fusion domain binding peptide from the HIV-1 envelope glycoprotein GP41. Biochem. Biophys. Res. Commun. 195, 533-538.

Jonak, Z. L., Clark, R. K., Matour, D., Trulli, S., Craig, R., Henri, E., Lee, E. V., Greig, R., and Debouck, C. (1993). A human lymphoid recombinant cell line with functional human immunodeficiency virus type envelope. AIDS Res. Hum. Retroviruses, 9: 23-32.

Kowalski, M., Potz, J, Basiripour, L., Dorfman, T, Goh, W C., Terwilliger, Dayton, A, Rosen, C., Haseltine, W, and Sodroski, J (1987). Functional regions of the envelope glycoprotein of human immunodeficiency virus type 1. Science 237, 1351-1355.

Krumbiegel, M., Herrmann, A, and Blumenthal, R. (1994). Kinetics of the low-pH induced conformational changes and fusogenic activity of influenza hemagglutinin. Biophys. J. 67, 2355-2360.

LaCasse, R. A, Follis, K. E., Trahey, M., Scarborough, J. D., Littman, D. R., and Nunberg, J H. (1999). Fusion-competent vaccines: Broad neutralization of primary isolates of HIV. Science 283, 357-362.

Liao, Z., Roos, J. W., and Hildreth, J. E. (2000). Increased infectivity of HIV type 1 particles bound to cell surface and solid-phase ICAM-1 and VCAM-1 through acquired adhesion molecules LFA-1 and VLA-4. AIDS Res. Hum. Retroviruses 16, 355-366.

Lifson, J D., Feinberg, M. B., Reyes, G. R., Rabins, L., Banapour, B. Chakrabarti, S., Moss, B., Wong-Staal, F., Steimer, K. S., and Engleman, E. G. (1986). Induction of CD4-dependent cell fusion by the HTLV-III/LAV envelope glycoprotein. Nature 323, 725-728.

Melikyan, G. B., Markosyan, R. M., Hemmati, H., Delmedico, M. K., Lambert, D. M., and Cohen, F. S. (2000). Evidence that the transition of HIV-1 gp41 into a six-helix bundle, not the bundle configuration, induces membrane fusion. J. Cell Biol. 151: 413-423.

Merezhinskaya, N., Kuijpers, G. A, and Raviv, Y. (1998). Reversible penetration of alpha-glutathione S-transferase into biological membranes revealed by photosensitized labeling in situ. Biochem. J. 335, 597-604.

Munoz-Barroso, I., Durell, S., Sakaguchi, K., Appella, E., and Blumenthal, R. (1998). Dilation of the human immunodeficiency virus-1 envelope glycoprotein fusion pore revealed by the inhibitory action of a synthetic peptide from gp41. J. Cell Biol. 140, 315-323.

Ott, D. E., Nigida, S. M., Jr., Henderson, L. E, and Arthur, L. O. (1995). The majority of cells are superinfected in a cloned cell line that produces high levels of human immunodeficiency virus type 1 strain MN. J. Virol. 69, 2443-2450.

Pak, C. C., Krumbiegel, M., Blumenthal, R., and Raviv, Y. (1994). Detection of influenza hemagglutinin interaction with biological membranes by photosensitized activation of [$^{125}$I]Iodonaphthylazide. J. Biol. Chem. 269, 14614-14619.

Pak, C. C., Puri, A., and Blumenthal, R. (1997). Conformational changes and fusion activity of vesicular stomatitis virus glycoprotein: [$^{125}$I]Iodonaphthylazide photo labeling studies in biological membranes. Biochemistry 36, 8890-8896.

Raviv, Y., Bercovici, T. and Salomon, Y. (1984) Biochemistry 23: 503-508.

Raviv, Y., Bercovici, T., Gitler, C., and Salomon, Y. (1989). Detection of nearest neighbors to specific fluorescently tagged ligands in rod outer segment and lymphocyte plasma membranes by photosensitization of 5-iodonaphthyl 1-azide. Biochemistry 28, 1313-1319.

Raviv, Y., Pollard, H. B., Bruggemann, E. P., Pastan, I., and Gottesman, M. M. (1990). Photosensitized labeling of a functional multidrug transporter in living drug-resistant tumor cells. J. Biol. Chem. 265, 3975-3980.

Raviv, Y., Puri, A., and Blumenthal, R. (2000). P-glycoprotein-overexpressing multidrug-resistant cells are resistant to infection by enveloped viruses that enter via the plasma membrane. FASEB J. 14: 511-515.

Raviv, Y., Salomon, Y., Gitler, C., and Bercovici, T. (1987). Selective labeling of proteins in biological systems by photosensitization of iodonaphthalene-1-azide. Proc. Natl. Acad. Sci. USA 84, 6103-6107.

Raviv, Y., Viard, M., Bess Jr., J. and Blumenthal, R. (2002) Virology 293: 243-351.

Rossio, J. L., Esser, M. T, Suryanarayana, K., Schneider, D. K., Bess, J. W., Jr., Vasquez, G. M., Wiltrout, T. A, Chertova, E., Grimes, M. K., Sattentau, Q., Arthur, L. O., Henderson, L. E., and Lifson, J D. (1998). Inactivation of human immunodeficiency virus type 1 infectivity with preservation of conformational and functional integrity of virion surface proteins. J. Virol. 72: 7992-8001.

Ugolini, S., Mondor, I., and Sattentau, Q. J. (1999). HIV-1 attachment: Another look. Trends Microbiol. 7: 144-149.

Volsky, D. J. (1990). Fusion of human immunodeficiency virus type 1 (HIV-1) with human cells as measured by membrane fluorescence dequenching (DQ) method: Roles of HIV-cell fusion in AIDS pathogenesis. In "Horizons in Membrane Biotechnology," pp. 179-198, Wiley-Liss, New York.

Weissenhorn, W., Dessen, A., Harrison, S. C., Skehel, J. J, and Wiley, D. C. (1997). Atomic structure of the ectodomain from HIV-1 gp41. Nature 387, 426-428.

Wild, C., Greenwell, T, and Matthews, T (1993). A synthetic peptide from HIV-1 gp41 is a potent inhibitor of virus-mediated cell-cell fusion. AIDS Res. Hum. Retroviruses 9, 1051-1053.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of inactivating an influenza virus comprising contacting the influenza virus with an effective amount of 1,5-iodonaphthylazide to form a mixture of the influenza virus and the 1,5-iodonaphthylazide, and exposing the mixture to light, optionally with an effective amount of a photo sensitizer chromophore, for a time sufficient to generate the inactivated influenza virus.

2. The method of claim 1, wherein the light is ultraviolet light.

3. The method of claim 1, wherein the light is visible light and an effective amount of a photosensitizer chromophore is included in the mixture.

4. The method of claim 1, wherein the inactivated influenza virus does not infect mammalian cells.

5. The method of claim 1, wherein the inactivated influenza virus is an effective vaccine against influenza infection in a mammal.

* * * * *